United States Patent
Mendell et al.

(10) Patent No.: US 8,466,117 B2
(45) Date of Patent: Jun. 18, 2013

(54) COMPOSITIONS AND METHODS FOR MODULATING ANGIOGENESIS

(75) Inventors: Joshua T. Mendell, Baltimore, MD (US); Erik A. Wentzel, Millersville, MD (US); Andrei Thomas-Tikhonenko, Philadelphia, PA (US); Michael Dews, Haddonfield, NJ (US); Asal Homayouni, Philadelphia, PA (US)

(73) Assignees: The Johns Hopkins University, Baltimore, MD (US); The Trustees of the University of Pennsylvania, Philadelphia, PA (US)

( * ) Notice: Subject to any disclaimer, the term of this patent is extended or adjusted under 35 U.S.C. 154(b) by 623 days.

(21) Appl. No.: 12/309,788

(22) PCT Filed: Jul. 30, 2007

(86) PCT No.: PCT/US2007/017085
§ 371 (c)(1),
(2), (4) Date: Mar. 15, 2010

(87) PCT Pub. No.: WO2008/014008
PCT Pub. Date: Jan. 31, 2008

(65) Prior Publication Data
US 2010/0184821 A1    Jul. 22, 2010

Related U.S. Application Data

(60) Provisional application No. 60/834,252, filed on Jul. 28, 2006.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ........................................ 514/44 A; 536/24.5

(58) Field of Classification Search
USPC .......................................... 514/44; 536/24.5
See application file for complete search history.

(56) References Cited

FOREIGN PATENT DOCUMENTS

| WO | WO-02/083862 | 10/2002 |
|---|---|---|
| WO | WO-2006/133022 | 12/2006 |
| WO | WO-2007/149521 | 12/2007 |
| WO | WO-2008/088858 | 7/2008 |

OTHER PUBLICATIONS

Daniel et al., American Journal of Pathology, 163(3):1185-1192 (2003).
Dews et al., Nature Genetics, 38(9): 1060-1066 (2006).
Matsubara et al., Oncogene, 26:6099-6105 (2007).

*Primary Examiner* — Terra Cotta Gibbs
(74) *Attorney, Agent, or Firm* — Edwards Wildman Palmer LLP; Peter F. Corless, Esq.; Richard B. Emmons

(57) ABSTRACT

The invention generally features compositions and methods that are useful for modulating angiogenesis.

11 Claims, 19 Drawing Sheets

COMPOSITIONS AND METHODS FOR MODULATING ANGIOGENESIS

CROSS-REFERENCE TO RELATED APPLICATION

This application claims the benefit of the following U.S. Provisional Application No. 60/834,252, which was filed on Jul. 28, 2006, the entire disclosure of which is hereby incorporated in its entirety.

BACKGROUND OF THE INVENTION

MicroRNAs (miRNAs) are 21-23 nucleotide RNA molecules that regulate the stability or translational efficiency of target mRNAs. miRNAs have diverse functions including the regulation of cellular differentiation, proliferation, and apoptosis. Although strict tissue- and developmental-stage-specific expression is critical for appropriate miRNA function, few mammalian transcription factors that regulate miRNAs have been identified.

Angiogenesis refers to the formation of new blood vessels, and is essential to proper embryonic development and growth, and tissue repair. Angiogenesis is also essential to many pathological conditions, including neoplasia, coronary artery disease, vascular disease, rheumatoid arthritis, psoriasis, and diabetic retinopathy.

Accordingly, improved compositions and methods for the prevention of angiogenesis and angiogenesis related diseases and disorders are required.

SUMMARY OF THE INVENTION

As described below, the present invention features compositions and methods for modulating angiogenesis in a subject.

In one aspect, the invention generally features a method of reducing angiogenesis (e.g., by at least about 5%, 10%, 25%, 50%, 75%, or 100%), the method comprising contacting a cell (e.g., a human cell in vitro or in vivo) with an effective amount of an inhibitory nucleic acid molecule (e.g., antisense or siRNA) complementary to at least a portion of a microRNA nucleic acid molecule of the mir-17-92 cluster (e.g., any one or more of mir-17-5p, mir-18a, mir-19a, mir-20a, mir-19b-1, and mir-92-1), thereby reducing angiogenesis. In one embodiment, the inhibitory nucleic acid molecule decreases the expression of the microRNA in the cell. In another embodiment, the cell is present in a tissue or organ. In yet another embodiment, the cell is a neoplastic cell or an ocular cell. In another embodiment, the cell is contacted with at least two, three, four, five or six inhibitory nucleic acid molecules. In yet another embodiment, the inhibitory nucleic acid molecules reduce the expression of mir-19 and mir-18. In yet another embodiment, the method increases expression of Tsp1 or CTGF relative to a reference (e.g., the level of Tsp1 or CTGF expression in the cell, tissue, or organ prior to treatment or the level present in a corresponding healthy or neoplastic control cell, tissue, or organ). In yet another embodiment, the TSR protein is selected from the group consisting of thrombospondin type 1 repeats (TSR): spondin-1 (f-spondin), thrombospondin-1, ADAMTS2, WISP2, thrombospondin repeat-containing protein 1, clusterin, connective tissue growth factor (CTGF), secreted acidic cysteine rich glycoprotein (SPARC), ADAMTS12, thrombospondin type I domain-containing protein 6. In yet another embodiment, the TSR protein is selected from the group consisting of thrombospondin type 1 repeats (TSR): CTGF, THSD3, ADAMTS18, ADAMTS12, THBS1, THSD1, ADAMTS1, ADAMTS6, WISP2, and BAI3. In still another embodiment, the antisense nucleic acid molecule comprises a nucleobase sequence having at least 85%, 90%, or 95% identity to a sequence selected from any one or more of the following:

```
miR-17-5p:    ACUACCUGCACuGUAAGCACUUUG;

mir-18a:      UAUGUGCACUAGAUGCACCUUA;

mir-19a:      UCAGUUUUGCAUAGAUUUGCACA;

mir-19b:      UCAGUUUUGCAUGGAUUUGCACA;

mir-20a:      CUACCUGCACUAUAAGCACUUUA;
and mir-92-1:     CAGGCCGGGACAAGUGCAAUA.
```

In other embodiments, the inhibitory nucleic acid molecule consists substantially of any one of those sequences.

In another aspect, the invention provides a method for increasing the expression of a TSR protein in a cell, the method comprising contacting the cell with an effective amount of an inhibitory nucleic acid molecule complementary to at least a portion of a microRNA nucleic acid molecule of the mir-17-92 cluster, thereby increasing the expression of a TSR protein. In one embodiment, the contact increases expression of a thrombospondin type 1 repeat (TSR) protein (e.g., Tsp1 or CTGF) relative to a reference.

In yet another aspect, the invention features a method of treating an apoptosis resistant neoplasm or chemo-resistant neoplasm in a subject. The method involves identifying a subject as having an apoptosis resistant neoplasm; and administering to the subject an effective amount of an inhibitory nucleic acid molecule complementary to at least a portion of a microRNA of the mir-17-92 cluster.

In yet another aspect, the invention features a method of treating or preventing a neoplasm in a subject in need thereof, the method involving identifying a neoplasm having an increase in the expression of a TSR protein; and administering to the subject an effective amount of an inhibitory nucleic acid molecule complementary to at least a portion of a microRNA of the mir-17-92 cluster.

In still another aspect, the invention features a method of treating an ocular disease characterized by increased angiogenesis in a subject, the method comprising administering to the subject an effective amount of an inhibitory nucleic acid molecule complementary to at least a portion of a microRNA of the mir-17-92 cluster. In one embodiment, the ocular disease is macular degeneration, age-related macular degeneration, choroidal neovascularization, or diabetic retinopathy.

In yet another aspect, the invention provides a method of characterizing a tumor as amenable to treatment with the method of previous aspect, the method comprising assaying the expression of a microRNA encoded by the miR-17-92 cluster.

In another aspect, the invention provides a method of characterizing a tumor as amenable to treatment, the method comprising assaying the expression of a TSR protein. In one embodiment, the method detects an increase or a decrease in the expression of a TSR protein relative to a reference.

In yet another aspect, the invention features a method of selecting a treatment for a subject having a neoplasm, the method involving detecting an increase the expression of a microRNA encoded by a mir-17-92 cluster or a TSR protein; and identifying the patient as having a neoplasm amenable to treatment with an inhibitory nucleic acid molecule that reduces the expression of a microRNA of the miR-17-92 cluster. In one embodiment, the method detects an increase in the expression of a microRNA and a TSR protein.

In another aspect, the invention provides a method of monitoring the treatment of a subject having a neoplasia, the method involving assaying the expression of a TSR protein in a cell of the subject and detecting an increase or a decrease in the expression of a TSR protein relative to a reference. In one embodiment, an increase in the expression of the TSR protein indicates that the treatment is beneficial.

In yet another aspect, the invention features an isolated nucleic acid molecule having at least 85%, 90%, 95% or greater nucleic acid sequence identity to a microRNA encoded by the miR-17-92 cluster, wherein expression of the nucleic acid molecule in a cell enhances angiogenesis. In one embodiment, the nucleic acid molecule has at least 85%, 90%, 95% or greater sequence identity to (human) a microRNA selected from the group consisting of miR-17-92, miR-19, and miR-18. In other embodiments, the nucleic acid molecule comprises at least one or more modifications, such as a non-natural internucleotide linkage, modified backbone, substituted sugar moiety, or cholesterol conjugation.

In another aspect, the invention provides an expression vector (e.g., a retroviral, adenoviral, adeno-associated viral, or lentiviral vector) encoding a nucleic acid molecule of any previous aspect. In one embodiment, the vector contains a promoter suitable for expression in a mammalian cell, wherein the promoter is operably linked to the nucleic acid molecule.

In another aspect, the invention provides a cell (e.g., a human cell in vivo or in vitro) containing the vector of the previous aspect or a nucleic acid molecule of any previous aspect. In one embodiment, the cell is a neoplastic colonocyte cell in vivo. In another embodiment, the cell is apoptosis-resistant or chemotherapy resistant.

In yet another aspect, the invention features method of enhancing angiogenesis, the method comprising contacting the cell with an effective amount of a nucleic acid molecule comprising at least a portion of a microRNA nucleic acid molecule of the mir-17-92 cluster. In one embodiment, the cell further expresses one or more of a thrombospondin family protein.

In another aspect, the invention provides a method of identifying an agent that reduces angiogenesis, the method involving contacting a cell that expresses a TSR selected from the group consisting of: Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), A disintegrin and metalloproteinase with Tsp motifs 6 (ADAMTS6), WNT1 inducible signaling pathway protein 2 (WISP2), and Brain-specific angiogenesis inhibitor 3 (BAI3) and a microRNA of the mir-17-92 cluster with a test agent; and detecting an increase in the level of TSR expression in the cell contacted by the agent with the level present in a control cell, wherein the increase in TSR expression identifying the agent as reducing angiogenesis.

In yet another aspect, the invention provides a method of identifying an agent that treats or prevents an apoptosis resistant neoplasm, the method comprising contacting a cell that expresses a microRNA of the mir-17-92 cluster with an agent, and detecting a reduction in the level of microRNA expression in the cell contacted by the agent with the level of expression in a control cell, wherein an agent that decreases microRNA expression thereby treats or prevents a neoplasm.

In various embodiments, the cell further expresses reduced levels of a TSR protein that is any one or more of Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), A disintegrin and metalloproteinase with Tsp motifs 6 (ADAMTS6), WNT1 inducible signaling pathway protein 2 (WISP2), and Brain-specific angiogenesis inhibitor 3 (BAI3) relative to a reference cell. In one embodiment, the decrease in expression is by at least about 5%, 10%, 15%, 25%, 30%, 50%, 75% or more.

In another aspect, the invention provides a method for diagnosing a subject as having or having a propensity to develop an apoptosis resistant neoplasia, the method involving measuring the level of a TSR protein selected from any one or more of Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), A disintegrin and metalloproteinase with Tsp motifs 6 (ADAMTS6), WNT1 inducible signaling pathway protein 2 (WISP2), and Brain-specific angiogenesis inhibitor 3 (BAI3) in a biological sample from the subject; and comparing the level of the TSR protein in the subject to the level present in a control subject, wherein a reduced level of TSR protein indicates the subject has or has a propensity to develop an apoptosis resistant neoplasia.

In another aspect, the invention provides a method for diagnosing a subject as having or having a propensity to develop an apoptosis resistant neoplasia, the method involving measuring the level of a mir17-92 encoded microRNA in a biological sample derived from a subject; and detecting an increased level of the microRNA relative to the level present in a control sample, wherein a, wherein an increase in the level of the mir-17-92 encoded microRNA indicates the subject has or has a propensity to develop a an apoptosis resistant neoplasia. In one embodiment, the level of mir-17-92 is detected in a microarray assay, an immunoassay, or a radioassay. In another embodiment, the method comprises measuring the level of nucleic acid molecule or polypeptide.

In yet another aspect, the invention features a pharmaceutical composition or kit for treating an apoptosis resistant neoplasm in a subject comprising an effective amount of an inhibitory nucleic acid molecule that is complementary to at least a fragment of mir-17-92 in a pharmaceutically acceptable excipient.

In various embodiments of any of the previous aspects, the TSR protein is Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), A disintegrin and metalloproteinase with Tsp motifs 6 (ADAMTS6), WNT1 inducible signaling pathway protein 2 (WISP2), and Brain-specific angiogenesis inhibitor 3 (BAI3). In other embodiments, the reference is the level of Tsp1 or CTGF expression in the cell prior to treatment or the level present in a corresponding neoplastic control cell. In still other embodiments, the inhibitory nucleic acid molecule is an antisense and siRNA nucleic acid molecule. In yet other embodiments, the antisense nucleic acid molecule comprises a nucleobase sequence having at least 85%, 90% or 95% identity to a sequence selected from any one or more (e.g., two, three, four, five or six) of the following:

| | |
|---|---|
| miR-17-5p: | ACUACCUGCACuGUAAGCACUUUG; |
| mir-18a: | UAUGUGCACUAGAUGCACCUUA; |
| mir-19a: | UCAGUUUUGCAUAGAUUUGCACA; |
| mir-19b: | UCAGUUUUGCAUGGAUUUGCACA; |
| mir-20a: and | CUACCUGCACUAUAAGCACUUUA; |
| mir-92-1: | CAGGCCGGGACAAGUGCAAUA. |

In still other embodiments of the above aspects, the cell is a neoplastic cell or an ocular cell. In other embodiments, the method increases expression of Tsp1 or CTGF relative to a reference. In yet other embodiments, the reference is the level of Tsp1 or CTGF expression in the cell prior to treatment or the level present in a corresponding neoplastic control cell. In other embodiments, the inhibitory nucleic acid molecule is an antisense and siRNA nucleic acid molecule. In still other embodiments, the cell is contacted with at least two, three, four, five, or six inhibitory nucleic acid molecules. In other embodiments, the inhibitory nucleic acid molecules reduce the expression of mir-19 and mir-18. In yet other embodiments of the previous aspects, the one or more inhibitory nucleic acid molecules are administered concurrently or within 14 days of each other in amounts sufficient to inhibit the growth of the apoptosis resistant neoplasm. In other embodiments of the above aspects, the neoplasm is selected from the group consisting of lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer. In still other embodiments of the above aspects, the inhibitory nucleic acid molecule is administered at in an amount between about 100 to 300 mg/m$^2$/day. In still other embodiments, the inhibitory nucleic acid molecule is administered systemically or locally to a subject. In still other embodiments, the method of administration targets the tumor and/or the tumor microenvironment (e.g., stromal cells, fibroblasts, endothelial cells, inflammatory cells, smooth muscle cells, and pericytes).

Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a polypeptide, polynucleotide, or fragment, or analog thereof, small molecule, or other biologically active molecule.

By "alteration" is meant a change (increase or decrease) in the expression levels of a gene or polypeptide as detected by standard art known methods such as those described above. As used herein, an alteration includes a 10% change in expression levels, preferably a 25% change, more preferably a 40% change, and most preferably a 50% or greater change in expression levels.

By "antisense molecule" is meant a non-enzymatic nucleic acid molecule or analog or variant thereof that binds to a target nucleic acid molecule sequence by means of complementary base pairing, such as an RNA-RNA or RNA-DNA interactions and alters the expression of the target sequence. Typically, antisense molecules are complementary to a target sequence along a single contiguous sequence of the antisense molecule. In certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of a target sequence.

The phrase "in combination with" is intended to refer to all forms of administration that provide an inhibitory nucleic acid molecule together with a second agent, such as a second inhibitory nucleic acid molecule or a chemotherapeutic agent, where the two are administered concurrently or sequentially in any order.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "complementary" is meant capable of pairing to form a double-stranded nucleic acid molecule or portion thereof. In one embodiment, an antisense molecule is in large part complementary to a target sequence. The complementarity need not be perfect, but may include mismatches at 1, 2, 3, or more nucleotides.

By "control" is meant a standard or reference condition.

By "corresponds" is meant comprising at least a fragment of a double-stranded gene, such that a strand of the double-stranded inhibitory nucleic acid molecule is capable of binding to a complementary strand of the gene.

By "decreases" is meant a reduction by at least about 5% relative to a reference level. A decrease may be by 5%, 10%, 15%, 20%, 25% or 50%, or even by as much as 75%, 85%, 95% or more.

By "an effective amount" is meant the amount of an agent required to ameliorate the symptoms of a disease or slow, stabilize, prevent, or reduce the severity of the pathology in a subject relative to an untreated subject. The effective amount of active agent(s) used to practice the present invention for therapeutic treatment of a neoplasia varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion (e.g., at least 5, 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference A "host cell" is any prokaryotic or eukaryotic cell that contains either a cloning vector or an expression vector. This term also includes those prokaryotic or eukaryotic cells that have been genetically engineered to contain the cloned gene (s) in the chromosome or genome of the host cell.

By "inhibitory nucleic acid molecule" is meant a single stranded or double-stranded RNA, siRNA (short interfering RNA), shRNA (short hairpin RNA), or antisense RNA, or a portion thereof, or an analog or mimetic thereof, that when administered to a mammalian cell results in a decrease (e.g., by 10%, 25%, 50%, 75%, or even 90-100%) in the expression (e.g., transcription or translation) of a target sequence. Typically, a nucleic acid inhibitor comprises or corresponds to at least a portion of a target nucleic acid molecule, or an ortholog thereof, or comprises at least a portion of the complementary strand of a target nucleic acid molecule.

By "marker" is meant any protein or polynucleotide having an alteration in expression level or activity that is associated with a disease or disorder.

The term "microarray" is meant to include a collection of nucleic acid molecules or polypeptides from one or more organisms arranged on a solid support (for example, a chip, plate, or bead).

By "miR-17-92 cluster" is meant the cluster of microRNAs located on chromosome 13 that encodes miRs-17-5p, 18a, 19a, 20a, 19-b1, and 92-1. The sequence of the primary transcript containing all the microRNAs present in the cluster is provided at GenBank Accession No. AB 176708.

By "mir-17-5p" is meant a microRNA comprising or having at least 85% identity to the nucleic acid sequence provided at Genbank Accession No. AF480529.

By "mir-18a" is meant a microRNA comprising or having at least 85% identity to the nucleic acid sequence provided at GenBank Accession No. AJ421736.

By "mir-19a" is meant a microRNA comprising or having at least 85% identity to the nucleic acid sequence provided at GenBank Accession No. AJ421737.

By "mir-20a" is meant a microRNA comprising or having at least 85% identity to the nucleic acid sequence provided at Genbank Accession No. AJ421738.

By "mir-19b-1" is meant a microRNA comprising or having at least 85% identity to the nucleic acid sequence provided at Genbank Accession No. AJ421739.

By "mir-92-1" is meant a microRNA comprising or having at least 85% identity to the nucleic acid sequence provided at Genbank Accession No. AF480530.

By "modification" is meant any biochemical or other synthetic alteration of a nucleotide, amino acid, or other agent relative to a naturally occurring reference agent.

By "neoplasia" is meant any disease that is caused by or results in inappropriately high levels of cell division, inappropriately low levels of apoptosis, or both. For example, cancer is a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

By "obtaining" as in "obtaining the inhibitory nucleic acid molecule" is meant synthesizing, purchasing, or otherwise acquiring the inhibitory nucleic acid molecule.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "positioned for expression" is meant that the polynucleotide of the invention (e.g., a DNA molecule) is positioned adjacent to a DNA sequence that directs transcription and translation of the sequence (i.e., facilitates the production of, for example, a recombinant microRNA molecule described herein).

By "portion" is meant a fragment of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 6, 7, 8, 9, 10, 11, 12, 13, 14, 15, 16, 17, 18, 19, 20, or 21 nucleotides.

By "reference" is meant a standard or control condition.

By "reporter gene" is meant a gene encoding a polypeptide whose expression may be assayed; such polypeptides include, without limitation, glucuronidase (GUS), luciferase, chloramphenicol transacetylase (CAT), and beta-galactosidase.

The term "siRNA" refers to small interfering RNA; a siRNA is a double stranded RNA that "corresponds" to or is complementary to a reference or target gene sequence. This matching need not be perfect so long as each strand of the siRNA is capable of binding to at least a portion of the target sequence. SiRNA can be used to inhibit gene expression, see for example Bass, 2001, Nature, 411, 428 429; Elbashir et al., 2001, Nature, 411, 494 498; and Zamore et al., Cell 101:25-33 (2000).

The term "subject" is intended to include vertebrates, preferably a mammal. Mammals include, but are not limited to, humans.

The term "pharmaceutically-acceptable excipient" as used herein means one or more compatible solid or liquid filler, diluents or encapsulating substances that are suitable for administration into a human.

By "specifically binds" is meant a molecule (e.g., peptide, polynucleotide) that recognizes and binds a protein or nucleic acid molecule of the invention, but which does not substantially recognize and bind other molecules in a sample, for example, a biological sample, which naturally includes a protein of the invention.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and still more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "TSR protein" is meant a thrombospondin type 1 repeats (TSR) containing protein or fragment thereof that modulates angiogenesis. Exemplary proteins include CTGF, THSD3, ADAMTS18, ADAMTS12, THBS1, THSD1, ADAMTS1, ADAMTS6, WISP2, and BAI3, and other proteins having at least 80%, 85%, 90%, 95% or greater amino acid sequence identity to such a protein.

By "targets" is meant alters the biological activity of a target polypeptide or nucleic acid molecule.

By "transformed cell" is meant a cell into which (or into an ancestor of which) has been introduced, by means of recombinant DNA techniques, a polynucleotide molecule encoding (as used herein) a protein of the invention.

By "vector" is meant a nucleic acid molecule, for example, a plasmid, cosmid, or bacteriophage, that is capable of replication in a host cell. In one embodiment, a vector is an expression vector that is a nucleic acid construct, generated recombinantly or synthetically, bearing a series of specified nucleic acid elements that enable transcription of a nucleic acid molecule in a host cell. Typically, expression is placed under the control of certain regulatory elements, including constitutive or inducible promoters, tissue-preferred regulatory elements, and enhancers.

BRIEF DESCRIPTION OF THE DRAWINGS

FIG. 1A is a graph showing the results of a cell accumulation assay performed on RasGfp and RasGfpMyc colonocytes. The number of viable cells in triplicate plates was assessed using the water-soluble tetrazolium-1 (WST) assay. The inset panel shows Myc overexpression detected by immunoblotting using mouse β-actin as a loading control. FIG. 1B is a graph showing the average weights of subcutaneous tumors formed by RasGfp (bars 1, 3, 4), RasGfpMyc (bar 2) and RasGfp-MycER (bars 5, 6) colonocytes. Where indicated, tumor-bearing animals were treated with 4-hydroxytamoxifen (4OHT) ('with 4OHT') or left untreated ('w/o 4OHT'). Error bars in FIGS. 1A and 1B refer to standard deviation (s.d.). FIG. 1C shows the results of immunostaining as a comparative analysis of RasGfp and RasGfp Myc tumors. The left panels are hematoxylin and eosin staining (H&E). Perfused blood vessels contain numerous red blood cells. The center panels show staining of endothelial cells with lectin (brown). The right panels show staining of lymphatic vessels with an antibody against LYVE-1 (brown). A large vessel in the RasGfpMyc LYVE-1 image localizes in the surrounding adipose tissue. The inset in the right panels depicts staining of normal ileum.

FIG. 2A is an immunoblot that shows lack of detectable HIF1a in RasGfp and RasGfpMyc tumor lysates. Two independent tumors of each type (T1 and T2) were assayed. Mouse embryonic stem (ES) cells cultured in the presence or absence of hypoxia mimetic desferrioxamine (DFX) were used for comparison. FIG. 2B shows ELISA-based quantification of VEGF A in the same neoplasms shown in FIG. 2A. FIG. 2C is a graph depicting the results of real-time RT-PCR analysis of thrombospondin-1 (thbs1) and connective tissue growth factor (CTGF) gene expression in the same neoplasms shown in FIG. 2A. Error bars refer to standard deviation (s.d.). FIG. 2D shows immunoblotting analysis of Tsp1 and CTGF expression levels. Cultured cells were used for CTGF detection. FIG. 2E shows immunoblotting analysis of CTGF expression levels in mass cultures of RasGfpMycER cells treated with 4OHT for the indicated number of hours. Whole-cell lysates and conditioned medium were analyzed. RasGfp and RasGfpMyc cells were used for comparison. FIG. 2F shows immunoblotting analysis as carried out in FIG. 2E performed on three single-cell RasGfpMycER clones. In the analysis of conditioned medium, thrombospondin type 1 repeat (TSR) protein levels were normalized to cell numbers. FIG. 2G shows immunoblotting analysis of Tsp1 and CTGF expression levels in RasGfpMycER clone 3. Assayed cells were initially treated with 4OHT for 72 hours (shown on the left) and then deprived of 4OHT for additional 72 hours (shown on the right). The trimeric form of Tsp1 was predominantly expressed in these lysates.

FIG. 3A shows real-time RT-PCR analysis of the miR-17-92 primary transcript. The same tumors were tested here as in FIG. 2. The upper panel depicts PCR products quantified in the bar graphs shown in the lower panel. Error bars refer to s.d. FIG. 3B shows RNA blot analysis of four RasGfp and four RasGfpMyc tumors. The miR-18 probe detects both pre-miR-18 and mature miR-18 species. U6 RNA was used as a loading control. Numbers below the autoradiogram refer to the increase in miR-18 levels as a multiple of that in RasGfp T1. FIG. 3C shows immunoblotting analysis of Tsp1 and CTGF expression levels in RasGfpMyc cells transfected with antisense 2'-O-methyl oligoribonucleotides targeting components of the miR-17-92 cluster. The left hand panel shows cells transfected with mixtures of scrambled or miR-17-92-specific oligoribonucleotides. Mock-transfected cells were used as an additional control. The panel on the right shows the same cells transfected with oligoribonucleotides targeting individual microRNAs. FIG. 3D shows the results of RT-PCR performed on Ras-only colonocytes transduced with either empty vector (RasPuro) or the miR-17-92-encoding retrovirus (RasPuroMIR). PCR primers were specific for the human miR-17-92 pre-miRNA and did not detect the endogenous mouse transcript. FIG. 3E shows RNA blot analysis of the same cells. RasGfp and RasGfpMyc cells were used for comparison. Other designations are the same as in FIG. 3B. FIG. 3F shows immunoblotting analysis of Tsp1 and CTGF expression levels in RasPuro versus RasPuroMIR cells.

FIG. 4A is a graph showing the results of a cell accumulation assay performed on RasPuro and RasPuroMIR colonocytes. Numbers of viable cells were assessed using the WST reagent as described in FIG. 1A. FIG. 4B is a graph showing the average sizes of subcutaneous tumors formed by RasPuro and RasPuroMIR colonocytes in syngeneic mice. "*" indicates statistical significance (P<0.05). P values were determined using unpaired Student's t-test. FIG. 4C is a graph showing the kinetics of tumor formation by RasPuro and RasPuroMIR colonocytes from experiment 2 in FIG. 4B. Error bars in 4A-4C represent s.d. FIG. 4D is a series of four panels showing immunostaining of blood perfused RasPuro and RasPuroMIR tumors. Immunofluorescent staining corresponds to FITC-conjugated lectin bound to vascular endothelial cells after intravenous injection. Two independent tumors were assayed. Representative 10× sections from each neoplasm are shown. FIG. 4E is two panels showing Matrigel neovascularization induced by the same cells as shown in FIG. 4D. The lower image shows richly perfused, large-caliber vascular channels that are typical of RasPuroMIR samples.

FIG. 5A is a Western Blot showing stable knock-down of c-Myc using shRNA. Cells were transduced with a lentivirus carrying an anti-Myc hairpin from the Sigma MISSION collection. A control shRNA-lentivirus was used as a negative control. The c-Myc, thrombo-spondin-1, and CTGF levels were assessed using Western blotting 4 days after infection. Actin was used as a loading control. FIG. 5B includes two graphs quantitating the results of real-time RT-PCR analysis of the miR-17-92 primary transcript. The same cells were tested as in FIG. 5A. Actin-specific PCR product was used as an internal control. FIG. 5C shows immunoflourescence experiments in the left hand panels and immunoblotting analysis in the right hand panels. In the immunoflourescence experiments, colon carcinoma cells were transfected with FITC-labeled oligonucleotides. The immunoblotting analysis shows Tsp1 levels in cells transfected with anti-sense 2'-O-methyl oligoribonucleotides targeting components of the miR-17-92 cluster. Scrambled oligo and mock-transfected cells were used as negative controls.

FIG. 6A shows expression levels of THBS1 and MYC in colon and, for comparison, CNS tumor cell lines. Individual cell lines are denoted on top. The blue-to-red transition corresponds to increasing mRNA levels. FIG. 6B shows down-regulation of THBS1 and upregulation of MYC mRNAs in human colon carcinoma samples, as compared to surrounding normal mucosas. Data from A. Levine's laboratory (Notterman et al., 2001) were analyzed using Oncomine 3.0 algorithm (available on the world wide web at oncomine.org).

DETAILED DESCRIPTION OF THE INVENTION

Figure 1A:
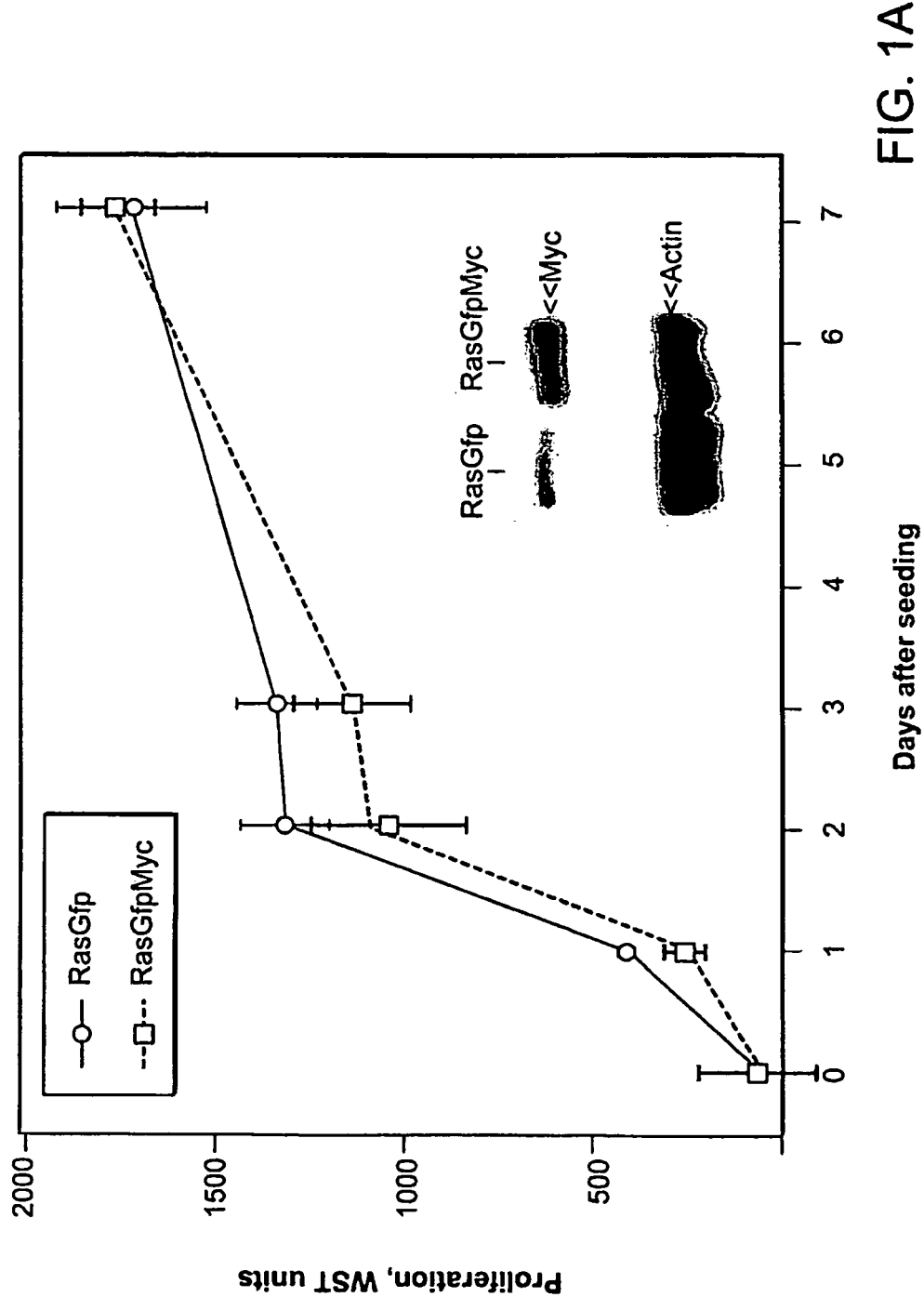
FIGS. 1A-1C show growth properties of RasGfp versus RasGfpMyc p53-null colonocytes in vivo and in vitro.

The invention generally features methods and compositions for modulating angiogenesis. In one embodiment, the invention features compositions and methods featuring inhibitory nucleic acid molecules (e.g., antisense oligonucleotides) that reduce or eliminate the expression of miRNAs whose expression enhances angiogenesis. Such inhibitory nucleic acid molecules are useful for the treatment of conditions characterized by an undesirable increase in angiogenesis (e.g., neoplasia, macular degeneration, diabetic retinopathy, acute inflammation). In particular embodiments, the invention provides compositions for the treatment of neoplasia, including apoptosis resistant neoplasia, which includes tumors that are resistant to chemotherapeutics, and neoplasia characterized by a decrease in the expression of one or more thrombospondin type 1 repeat (TSR) proteins (e.g., Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A Disintegrin and Metalloproteinase with Tsp motifs 1 (ADAMTS1), A disintegrin and metalloproteinase with Tsp motifs 6 (ADAMTS6), WNT1 inducible signaling pathway protein 2 (WISP2), and Brain-specific angiogenesis inhibitor 3 (BAI3)). In other embodiments, the invention provides compositions featuring polynucleotides comprising the nucleic acid sequence of a microRNA of the invention, and methods for using such polynucleotides to enhance angiogenesis for the treatment or prevention of conditions where an increase in angiogenesis would provide a therapeutic effect. Such conditions include, but are not limited to, ischemia, myocardial infarction, and poorly healing wounds.

MicroRNAs of the mir-17-92 Cluster

MicroRNAs (miRNAs) are 21-23 nucleotide RNA molecules that regulate the stability or translational efficiency of target mRNAs. miRNAs have diverse functions including the regulation of cellular differentiation, proliferation, and apoptosis (Ambros, *Nature* 431, 350-5 (2004)). Although strict tissue- and developmental-stage-specific expression is critical for appropriate miRNA function, few mammalian transcription factors that regulate miRNAs have been identified. The proto-oncogene c-MYC encodes a transcription factor that regulates cell proliferation, growth, and apoptosis (Levens, *Proc Natl Acad Sci USA* 99, 5757-9 (2002). Dysregulated expression or function of c-Myc is one of the most common abnormalities in human malignancy (Cole et al., *Oncogene* 18, 2916-24 (1999)). c-Myc activated expression of a cluster of six miRNAs on human chromosome 13.

Inhibitory and Recombinant Nucleic Acid Molecules

As described in more detail below, c-Myc activation of microRNAs of the mir-17-92 cluster is associated with angiogenesis. Accordingly, the invention provides compositions that modulate angiogenesis, as well as methods of using such compositions for the treatment of diseases where an increase or decrease in angiogenesis is beneficial. In one embodiment, the invention provides inhibitory nucleic acid molecules, such as antisense nucleic acid molecules, that decrease the expression of at least one microRNA of the miR-17-92 cluster. Inhibitory nucleic acid molecules are essentially nucleobase oligomers that may be employed to reduce the expression of a target nucleic acid sequence, such as a nucleic acid sequence that encodes a microRNA of the miR-17-92 cluster. The inhibitory nucleic acid molecules provided by the invention include any nucleic acid molecule sufficient to decrease the expression of a nucleic acid molecule of the miR-17-92 cluster by at least 5-10%, desirably by at least 25%-50%, or even by as much as 75%-100%. Each of the nucleic acid sequences provided herein may be used, for example, in the discovery and development of therapeutic antisense nucleic acid molecules to decrease the expression of a microRNA encoded by the miR-17-92 cluster (e.g., mir-17-5p or mir-20a). If desired, antisense nucleic acid molecules that target one or more microRNAs of the miR-17-92 cluster are administered in combination, such that the coordinated reduction in the expression of two or more microRNAs encoded by the miR-17-92 cluster is achieved.

The invention is not limited to antisense nucleic acid molecules, but encompasses virtually any single-stranded or double-stranded nucleic acid molecule that decreases expression of a microRNA within the miR-17-92 cluster. The invention further provides catalytic RNA molecules or ribozymes. Such catalytic RNA molecules can be used to inhibit expression of a microRNA nucleic acid molecule in vivo.

The inclusion of ribozyme sequences within an antisense RNA confers RNA-cleaving activity upon the molecule, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference. In various embodiments of this invention, the catalytic nucleic acid molecule is formed in a hammerhead or hairpin motif. Examples of such hammerhead motifs are described by Rossi et al., Nucleic Acids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In another approach, the inhibitory nucleic acid molecule is a double-stranded nucleic acid molecule used for RNA interference (RNAi)-mediated knock-down of the expression of a microRNA. siRNAs are also useful for the inhibition of microRNAs. See, for example, Nakamoto et al., Hum Mol Genet, 2005. Desirably, the siRNA is designed such that it provides for the cleavage of a target microRNA of the invention. In one embodiment, a double-stranded RNA (dsRNA) molecule is made that includes between eight and twenty-five (e.g., 8, 10, 12, 15, 16, 17, 18, 19, 20, 21, 22, 23, 24, 25) consecutive nucleobases of a nucleobase oligomer of the invention. The dsRNA can be two complementary strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. Double stranded RNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference. An inhibitory nucleic acid molecule that "corresponds" to a microRNA of the miR-17-92 cluster comprises at least a fragment of the double-stranded gene, such that each strand of the double-stranded inhibitory nucleic acid molecule is capable of binding to the complementary strand of the target gene. The inhibitory nucleic acid molecule need not have perfect correspondence or need not be perfectly complementary to the reference sequence. In one embodiment, an siRNA has at least about 85%, 90%, 95%, 96%, 97%, 98%, or even 99% sequence identity with the target nucleic acid or has that degree of complementarity. For example, a 19 base pair duplex or single-stranded nucleic acid molecule having 1-2 base pair mismatch is considered useful in the methods of the invention. In other embodiments, the nucleobase sequence of the inhibitory nucleic acid molecule exhibits 1, 2, 3, 4, 5 or more mismatches.

Inhibitory nucleic acid molecules of the invention also include double stranded nucleic acid "decoys." Decoy molecules contain a binding site for a transcription factor that is responsible for the deregulated transcription of a gene of interest. The present invention provides decoys that competitively block binding to a regulatory element in a target gene (e.g., miR-17-92 cluster). The competitive inhibition of c-Myc binding by the decoy results in the indirect inhibition of transcription of a target microRNA of the miR-17-92 cluster. An overview of decoy technology is provided by Suda et al., Endocr. Rev., 1999, 20, 345-357; S. Yla-Hertttuala and J. F. Martin, The Lancet 355, 213-222, 2000). In one therapeutic method, short double-stranded DNA decoy molecules are introduced into cells of a subject. The decoys are provided in a form that facilitates their entry into target cells of the subject. Having entered a cell, the decoy specifically binds an endogenous microRNA, thereby competitively inhibiting the microRNA from binding to an endogenous gene. The decoys are administered in amounts and under conditions whereby binding of the endogenous microRNA to the endogenous gene is effectively competitively inhibited without significant host toxicity. Depending on the transcription factor, the methods can effect up- or down-regulation of gene expression. The subject compositions comprise the decoy molecules in a context that provides for pharmacokinetics sufficient for effective therapeutic use.

In other embodiments, the invention provides isolated microRNAs of the miR-17-92 cluster and polynucleotides comprising such sequences. A recombinant microRNA of the invention may be administered to enhance angiogenesis in a subject in need thereof. In one approach, the microRNA is administered as a naked RNA molecule. In another approach, it is administered in an expression vector suitable for expression in a mammalian cell.

Another therapeutic approach included in the invention involves administration of a recombinant therapeutic, such as a recombinant microRNA or an inhibitory nucleic acid molecule, variant, or fragment thereof, either directly to the site of a potential or actual disease-affected tissue or systemically (for example, by any conventional recombinant protein administration technique). The dosage of the administered microRNA depends on a number of factors, including the size and health of the individual patient. For any particular subject, the specific dosage regimes should be adjusted over time according to the individual need and the professional judgment of the person administering or supervising the administration of the compositions.

For example, a microRNA or an inhibitory nucleic acid molecule of the invention may be administered in dosages between about 1 and 100 mg/kg (e.g., 1, 5, 10, 20, 25, 50, 75, and 100 mg/kg). In other embodiments, the dosage ranges from between about 25 and 500 mg/m$^2$/day. Desirably, a human patient having a neoplasia receives a dosage between about 50 and 300 mg/m$^2$/day (e.g., 50, 75, 100, 125, 150, 175, 200, 250, 275, and 300). For the treatment of an ophthalmologic disease characterized by an undesired increase in angiogenesis (e.g., neochoroidal vascularization, age-related macular degeneration, diabetic retinopathy), compositions of the invention are administered in dosages between about 1 and 100 mg/kg (e.g., 1, 5, 10, 20, 25, 50, 75, and 100 mg/kg).

Modified Inhibitory Nucleic Acid Molecules

A desirable inhibitory nucleic acid molecule is one based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the IC$_{50}$. This modification also increases the nuclease resistance of the modified oligonucleotide. It is understood that the methods and reagents of the present invention may be used in conjunction with any technologies that may be developed to enhance the stability or efficacy of an inhibitory nucleic acid molecule.

Inhibitory nucleic acid molecules include nucleobase oligomers containing modified backbones or non-natural internucleoside linkages. Oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers. Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriest-ers, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Nucleobase oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleobase oligomer, particularly the 3' position of the sugar on the 3' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

In other nucleobase oligomers, both the sugar and the internucleoside linkage, i.e., the backbone, are replaced with novel groups. The nucleobase units are maintained for hybridization with a nucleic acid molecule of the miR-17-92 cluster. Methods for making and using these nucleobase oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In other embodiments, a single stranded modified nucleic acid molecule (e.g., a nucleic acid molecule comprising a phosphorothioate backbone and 2'-O-Me sugar modifications is conjugated to cholesterol. Such conjugated oligomers are known as "antagomirs." Methods for silencing microRNAs in vivo with antagomirs are described, for example, in Krutzfeldt et al., Nature 438: 685-689.

Delivery of Nucleobase Oligomers

Naked oligonucleotides are capable of entering tumor cells or of entering the stroma and inhibiting the expression or activity of a microRNA of the miR-17-92 cluster. Nonetheless, it may be desirable to utilize a formulation that aids in the delivery of an inhibitory nucleic acid molecule or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Polynucleotide Therapy

Polynucleotide therapy featuring a polynucleotide encoding a microRNA or an inhibitory nucleic acid molecule or analog thereof that targets a microRNA of the miR-17-92 cluster is another therapeutic approach for modulating angiogenesis in a subject. Expression vectors encoding the microRNAs or inhibitory nucleic acid molecules can be delivered to cells of a subject in need of increased or decreased angiogenesis. The nucleic acid molecules must be delivered to the cells of a subject in a form in which they can be taken up and are advantageously expressed so that therapeutically effective levels can be achieved.

Methods for delivery of the polynucleotides to the cell according to the invention include using a delivery system such as liposomes, polymers, microspheres, gene therapy vectors, and naked DNA vectors.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an inhibitory nucleic acid molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cometta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the introduction of an inhibitory nucleic acid molecule therapeutic to a cell of a patient diagnosed as having a neoplasia. For example, an inhibitory nucleic acid molecule that targets a microRNA of the miR-17-92 cluster can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247: 1465, 1990). Preferably the inhibitory nucleic acid molecules are administered in combination with a liposome and protamine.

Gene transfer can also be achieved using non-viral means involving transfection in vitro. Such methods include the use of calcium phosphate, DEAF dextran, electroporation, and protoplast fusion. Liposomes can also be potentially beneficial for delivery of DNA into a cell.

Inhibitory nucleic acid molecule expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers.

For any particular subject, the specific dosage regimes should be adjusted over time according to the individual need and the professional judgment of the person administering or supervising the administration of the compositions.

Pharmaceutical Compositions

As reported herein, an increase in the expression of microRNAs of the miR-17-92 cluster is associated with an increase in angiogenesis. Accordingly, the invention provides therapeutic compositions that decrease the expression of a microRNAs of the miR-17-92 cluster to reduce angiogenesis. In one embodiment, the present invention provides a pharmaceutical composition comprising an inhibitory nucleic acid molecule (e.g., an antisense, siRNA, or shRNA polynucleotide) that decreases the expression of one or more nucleic acid molecules encoded by the miR-17-92 cluster (e.g., mir-17-5p or mir-20a). If desired, the inhibitory nucleic acid molecule is administered in combination with a chemotherapeutic agent. In another embodiment, a recombinant microRNA of the miR-17-92 cluster, or a polynucleotide encoding such a microRNA, is administered to increase angiogenesis. Polynucleotides of the invention may be administered as part of a pharmaceutical composition. The compositions should be sterile and contain a therapeutically effective amount of the polypeptides or nucleic acid molecules in a unit of weight or volume suitable for administration to a subject.

A recombinant microRNA, an inhibitory nucleic acid molecule of the invention, or other regulator of a microRNA encoded by the miR-17-92 cluster (e.g., mir-17-5p or mir-20a) may be administered within a pharmaceutically-acceptable diluent, carrier, or excipient, in unit dosage form. Conventional pharmaceutical practice may be employed to provide suitable formulations or compositions to administer the compounds to patients suffering from a neoplasia (e.g., an apoptosis resistant neoplasia, or a neoplasia characterized by an increase in an angiogenic marker). Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a neoplastic or ischemic disease or condition. The preferred dosage of a nucleobase oligomer of the invention is likely to depend on such variables as the type and extent of the disorder, the overall health status of the particular patient, the formulation of the compound excipients, and its route of administration.

With respect to a subject having a neoplastic disease or disorder, an effective amount is sufficient to stabilize, slow, or reduce the proliferation of the neoplasm. Generally, doses of active polynucleotide compositions of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of an antisense targeting the miR-17-92 cluster (e.g., mir-17-5p or mir-20a).

Therapy

Therapy may be provided wherever cancer therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of neoplasia being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. As described above, if desired, treatment with an inhibitory nucleic acid molecule of the invention may be combined with therapies for the treatment of proliferative disease (e.g., radiotherapy, surgery, or chemotherapy). For any of the methods of application described above, an inhibitory nucleic acid molecule of the invention is desirably administered intravenously or is applied to the site of neoplasia (e.g., by injection).

Diagnostics

As described in more detail below, the present invention has identified increases in the expression of microRNAs of the miR-17-92 cluster and c-Myc, and in TSR protein markers that are associated with neoplasia. Neoplasias having increased levels of microRNAs, and/or reduced levels of a TSR protein, show increased aggressiveness due to enhanced angiogenesis. Thus, alterations in the expression level of one or more (e.g., 1, 2, 3, 4, 5, 6, 7, 8, 9, 10, 11, 12, 13, 14, 15, 16, 17, 18, 19, or 20) of the following markers is used to diagnose a subject as having a particularly aggressive neoplasia: mir-17-5p, mir-18a, mir-19a, mir-20a, mir-19b-1, mir-92-1, c-Myc, E2F1, p21, Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3). If desired, alterations in the expression of one, two, three, four, five, six, seven, eight, nine, ten, eleven, all of these markers is used to diagnose or characterize a neoplasia. In another embodiment, the method identifies a neoplasia as amenable to treatment using a method of the invention by assaying an increase in the level of any one or more of the following angiogenic markers: Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3). In one preferred embodiment, the invention characterizes a neoplasia as having an increase in thrombospondin and at least one additional protein of the miR-17-92 cluster or of an angiogeneic marker.

In one embodiment, a subject is diagnosed as having or having a propensity to develop a neoplasia, the method comprising measuring markers in a biological sample from a patient, and detecting an alteration in the expression of test marker molecules relative to the sequence or expression of a reference molecule. The markers typically include a microRNA of the miR-17-92 cluster together with c-Myc or with an angiogenic marker, such as Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3). While the following approaches describe diagnostic methods featuring a microRNA of the miR-17-92 cluster, the skilled artisan will appreciate that any one or more of the markers set forth above is useful in such diagnostic methods.

Increased expression of a microRNA of the miR-17-92 cluster or of a TSR protein marker is used to identify a neoplasia that is amenable to treatment using a composition or method described herein. Accordingly, the invention provides compositions and methods for identifying such neoplasias in a subject. Alterations in gene expression are detected using methods known to the skilled artisan and described herein. Such information can be used to diagnose a neoplasia or to identify a neoplasia as being amenable to a therapeutic method of the invention.

In one approach, diagnostic methods of the invention are used to assay the expression of a microRNA of the miR-17-92 cluster or a TSR protein in a biological sample relative to a reference (e.g., the level of microRNA of the miR-17-92 cluster or TSR present in a corresponding control tissue, such as a healthy tissue or a neoplastic tissue not exhibiting increased angiogenesis). In another approach, diagnostic methods of the invention are used to assay the expression of a marker. For example, the level of a microRNA of the miR-17-92 cluster is detected using a nucleic acid probe that specifically binds a microRNA of the miR-17-92 cluster. Exemplary nucleic acid probes that specifically bind a microRNA of the miR-17-92 cluster are described herein. By "nucleic acid probe" is meant any nucleic acid molecule, or fragment thereof, that binds a microRNA encoded by the miR-17-92 cluster. Such nucleic acid probes are useful for the diagnosis of a neoplasia.

In one approach, quantitative PCR methods are used to identify an increase in the expression of a microRNA encoded by the miR-17-92 cluster or a TSR protein. In another approach, PCR methods are used to identify an alteration in the sequence of a microRNA encoded by the miR-17-92 cluster or a TSR protein. The invention provides probes that are capable of detecting a microRNA encoded by the miR-17-92 cluster or a TSR protein. Such probes may be used to hybridize to a nucleic acid sequence derived from a patient having a neoplasia (e.g., a neoplasia having increased angiogenic capacity or apoptosis resistant). The specificity of the probe determines whether the probe hybridizes to a naturally occurring sequence, allelic variants, or other related sequences. Hybridization techniques may be used to identify mutations indicative of a neoplasia or may be used to monitor expression levels of these genes (for example, by Northern analysis (Ausubel et al., supra).

In yet another embodiment, an immunoassay, radioassay, or other quantitative assay is used to measure the level of an angiogenic marker, including Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3). The level of the marker is compared to the level present in a control sample (e.g., a normal tissue or a tumor sample isolated from a subject having a neoplasia that is not characterized by an increase in a mir-17 microRNA and/or an increase in the level of an angiogenic marker.

In general, the measurement of a nucleic acid molecule or a protein in a subject sample is compared with a diagnostic amount present in a reference. A diagnostic amount distinguishes between a neoplastic tissue and a control tissue. The skilled artisan appreciates that the particular diagnostic amount used can be adjusted to increase sensitivity or specificity of the diagnostic assay depending on the preference of the diagnostician. In general, any significant increase or decrease (e.g., at least about 10%, 15%, 30%, 50%, 60%, 75%, 80%, or 90%) in the level of test nucleic acid molecule or polypeptide in the subject sample relative to a reference may be used to diagnose or characterize a neoplasia. Test molecules include any one or more of mir-17-5p, mir-18a, mir-19a, mir-20a, mir-19b-1, mir-92-1, c-Myc, E2F1, p21, Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3). In one embodiment, the reference is the level of test polypeptide or nucleic acid molecule present in a control sample obtained from a patient that does not have a neoplasia. In another embodiment, the reference is a baseline level of test molecule present in a biologic sample derived from a patient prior to, during, or after treatment for a neoplasia. In yet another embodiment, the reference can be a standardized curve.

Types of Biological Samples

The level of markers in a biological sample from a patient having or at risk for developing a neoplasia can be measured, and an alteration in the expression of test marker molecule relative to the sequence or expression of a reference molecule, can be determined in different types of biologic samples. Test markers include any one or all of the following: mir-17-5p, mir-18a, mir-19a, mir-20a, mir-19b-1, mir-92-1, c-Myc, E2F1, p21, Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3). The biological samples are generally derived from a patient, preferably as a bodily fluid (such as blood, cerebrospinal fluid, phlegm, saliva, or urine) or tissue sample (e.g. a tissue sample obtained by biopsy).

Kits

The invention provides kits for the diagnosis or monitoring of a neoplasia, such as an apoptosis resistant neoplasia or a neoplasia having increased aggressiveness, due to enhanced angiogenesis or angiogenic potential. In one embodiment, the kit detects an alteration in the expression of a Marker (e.g., mir-17-5p, mir-18a, mir-19a, mir-20a, mir-19b-1, mir-92-1, c-Myc, E2F1, p21, Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3)) nucleic acid molecule relative to a reference level of expression. In another embodiment, the kit detects an alteration in the sequence of a miR-17-92 cluster nucleic acid molecule (e.g., a micrRNA of the cluster, such as mir-17-5p, mir-18a, mir-19a, mir-20a, mir-19b-1, mir-92-1) derived from a subject relative to a reference sequence. In related embodiments, the kit includes reagents for monitoring the expression of a miR-17-92 cluster nucleic acid molecule or a nucleic acid molecule encoding Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3), such as primers or probes that hybridize to a miR-17-92 cluster nucleic acid molecule.

Optionally, the kit includes directions for monitoring the nucleic acid molecule levels of a Marker in a biological sample derived from a subject. In other embodiments, the kit comprises a sterile container which contains the primer, probe, antibody, or other detection regents; such containers can be boxes, ampoules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a neoplasia. Preferably, the kit further comprises any one or more of the reagents described in the diagnostic assays described herein. In other embodiments, the instructions include at least one of the following: description of the primer or probe; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

Patient Monitoring

The disease state or treatment of a patient having a neoplasia can be monitored using the methods and compositions of the invention. In one embodiment, the disease state of a patient can be monitored using the methods and compositions of the invention. Such monitoring may be useful, for example, in assessing the efficacy of a particular drug in a patient. Therapeutics that alter the expression of any one or more of the Markers of the invention (e.g., mir-17-5p, mir-18a, mir-19a, mir-20a, mir-19b-1, mir-92-1, c-Myc, E2F1, p21, Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3)) are taken as particularly useful in the invention.

Screening Assays

One embodiment of the invention encompasses a method of identifying an agent that inhibits the expression or activity of a microRNA of the miR-17-92 cluster and/or the expression of a Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3). Accordingly, compounds that modulate the expression or activity of a miR-17-92 cluster or angiogenic marker nucleic acid molecule, variant, or portion thereof are useful in the methods of the invention for the treatment or prevention of a neoplasm (e.g., breast, colon, lymph, ovary, stomach, thyroid, testis, and uterine cancer). The method of the invention may measure a decrease in transcription of one or more microRNAs or angiogenic markers of the invention or an alteration in the transcription or translation of the target of such a microRNA (e.g., Connective tissue growth factor (CTGF), thrombospondin, type I domain containing 3 isoform 3 (THSD3), A disintegrin and metalloproteinase with Tsp motifs 18 (ADAMTS18), A disintegrin and metalloproteinase with Tsp motifs 12 (ADAMTS12), Thrombospondin 1 (THBS1), Thrombospondin, type 1 domain containing 1 (THSD1), A disintegrin and metalloproteinase with Tsp motifs 1 (ADAMTS1), a disintegrin and metalloproteinase with Tsp motifs 6 (ADAMTS6), WNT1 inducible signaling pathway protein 2 (WISP2), and Brain-specific angiogenesis inhibitor 3 (BAI3), p21, or E2F1). Any number of methods are available for carrying out screening assays to identify such compounds. In one approach, the method comprises contacting a cell that expresses a microRNA or angiogenic marker with an agent and comparing the level of expression in the cell contacted by the agent with the level of expression in a control cell, wherein an agent that decreases the expression of a miR-17-92 cluster microRNA expression or an angiogenic marker thereby inhibits a neoplasia. In another approach, candidate compounds are identified that specifically bind to and alter the activity of a microRNA of the invention. Methods of assaying such biological activities are known in the art and are described herein. The efficacy of such a candidate compound is dependent upon its ability to interact with a miR-17-92 cluster microRNA or angiogenic marker. Such an interaction can be readily assayed using any number of standard binding techniques and functional assays (e.g., those described in Ausubel et al., supra).

Potential agonists and antagonists of a miR-17-92 cluster microRNA or angiogenic marker include organic molecules, peptides, peptide mimetics, polypeptides, nucleic acid molecules (e.g., double-stranded RNAs, siRNAs, antisense polynucleotides), and antibodies that bind to a nucleic acid sequence or polypeptide of the invention and thereby inhibit or extinguish its activity. Potential antagonists also include small molecules that bind to the miR-17-92 cluster microRNA thereby preventing binding to cellular molecules with which the microRNA normally interacts, such that the normal biological activity of the miR-17-92 cluster microRNA is reduced or inhibited. Small molecules of the invention preferably have a molecular weight below 2,000 daltons, more preferably between 300 and 1,000 daltons, and still more preferably between 400 and 700 daltons. It is preferred that these small molecules are organic molecules.

Compounds that are identified as binding to a miR-17-92 cluster microRNA or angiogenic marker of the invention with an affinity constant less than or equal to 10 mM are considered particularly useful in the invention. Alternatively, any in vivo protein interaction detection system, for example, any two-hybrid assay may be utilized to identify compounds that interact with miR-17-92 cluster microRNA or angiogenic marker. Interacting compounds isolated by this method (or any other appropriate method) may, if desired, be further purified (e.g., by high performance liquid chromatography). Compounds isolated by any approach described herein may be used as therapeutics to treat a neoplasia in a human patient.

In addition, compounds that inhibit the expression of an miR-17-92 cluster microRNA or angiogenic marker whose expression is increased in a subject having a neoplasia are also useful in the methods of the invention. Any number of methods are available for carrying out screening assays to identify new candidate compounds that alter the expression of a miR-17-92 cluster microRNA or angiogenic marker. The invention also includes novel compounds identified by the above-described screening assays. Optionally, such compounds are characterized in one or more appropriate animal models to determine the efficacy of the compound for the treatment of a neoplasia. Desirably, characterization in an animal model can also be used to determine the toxicity, side effects, or mechanism of action of treatment with such a compound. Furthermore, novel compounds identified in any of the above-described screening assays may be used for the treatment of a neoplasia in a subject. Such compounds are useful alone or in combination with other conventional therapies known in the art.

Test Compounds and Extracts

In general, compounds capable of inhibiting the growth or proliferation of a neoplasia by decreasing the expression or biological activity of a miR-17-92 cluster microRNA (e.g., mir-17-5p or mir-17-20a) or angiogenic marker are identified from large libraries of either natural product or synthetic (or semi-synthetic) extracts or chemical libraries according to methods known in the art. Methods for making siRNAs are known in the art and are described in the Examples. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

In one embodiment, test compounds of the invention are present in any combinatorial library known in the art, including: biological libraries; peptide libraries (libraries of molecules having the functionalities of peptides, but with a novel, non-peptide backbone which are resistant to enzymatic degradation but which nevertheless remain bioactive; see, e.g., Zuckermann, R. N. et al., *J. Med. Chem.* 37:2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al, *Proc. Natl. Acad. Sci. U.S.A.* 90:6909, 1993; Erb et al, *Proc. Natl. Acad. Sci. USA* 91:11422, 1994; Zuckermann et al., *J. Med. Chem.* 37:2678, 1994; Cho et al, *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994.

Libraries of compounds may be presented in solution (e.g., Houghten, *Biotechniques* 13:412-421, 1992), or on beads (Lam, *Nature* 354:82-84, 1991), chips (Fodor, *Nature* 364: 555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-neoplastic activity should be employed whenever possible.

In an embodiment of the invention, a high throughput approach can be used to screen different chemicals for their potency to affect the activity of a miR-17-92 cluster microRNA (e.g., mir-17-5p or mir-17-20a) or an angiogenic marker.

Those skilled in the field of drug discovery and development will understand that the precise source of a compound or test extract is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

When a crude extract is found to alter the biological activity of a miR-17-92 cluster microRNA (e.g., mir-17-5p or mir-17-20a) or angiogenic marker variant, or fragment thereof, further fractionation of the positive lead extract is necessary to isolate chemical constituents responsible for the observed effect. Thus, the goal of the extraction, fractionation, and purification process is the careful characterization and identification of a chemical entity within the crude extract having anti-neoplastic activity. Methods of fractionation and purification of such heterogeneous extracts are known in the art. If desired, compounds shown to be useful agents for the treatment of a neoplasm are chemically modified according to methods known in the art.

The present invention further provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which a neoplasia may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

EXAMPLES

Example 1

Myc-Overexpressing Tumors Show Robust Neovascularization

The role of c-Myc in neovascularization of one-hit neoplasms has been established (1-4) and involves both upregulation of pro-angiogenic VEGF4-6 and downregulation of anti-angiogenic Tsp1 (7-9). To address the role of Myc in neovascularization of genetically complex tumors, p53-null mouse colonocytes were used. These cells can be transformed in vitro by low-grade over-expression of either activated K-Ras or Myc (10,11). When engrafted into syngeneic mice, subcutaneously or orthotopically (into the cecal wall), Ras-overexpressing cells formed tumors, but their Myc-overexpressing counterparts did not.

Figure 1B:
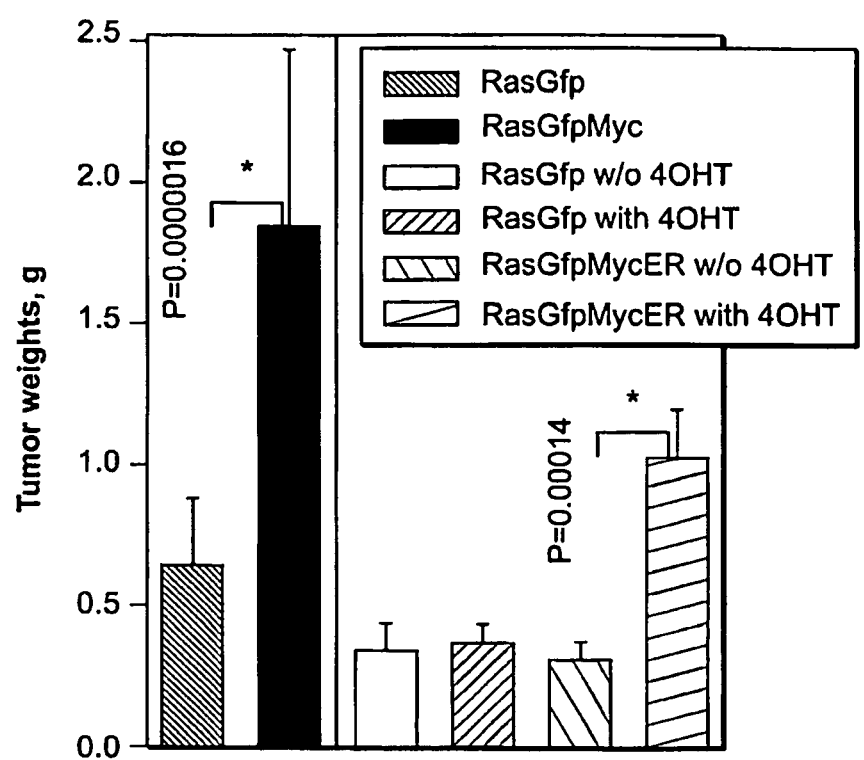

Next, MYC was introduced into ras-transformed colonocytes, either constitutively ('RasGfpMyc') or in a 4-hydroxytamoxifen (4OHT)-dependent form ('RasGfpMycER'). No increase in cell accumulation in vitro was observed as compared to Ras cells expressing GFP alone ('RasGfp') (FIG. 1A). Control RasGfp cells formed relatively small tumors. In contrast, RasGfpMyc neoplasms were on average three times larger (FIG. 1B). The same increase in tumor sizes was observed with RasGfpMycER cells in animals continuously treated with 4OHT (FIG. 1B).

Figure 1C:
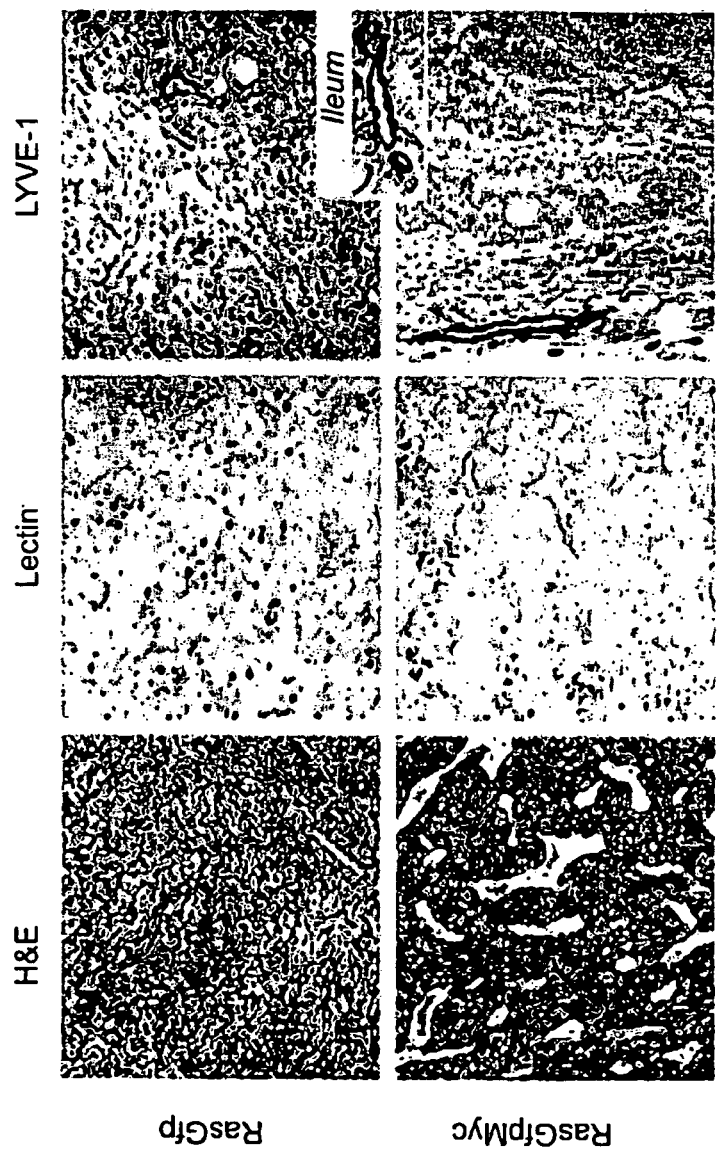

To determine the contribution of Myc to neoplastic growth, histological examination of size-matched tumors was carried out. Myc-overexpressing tumors possessed much more robust neovascularization. Especially numerous were large-caliber vessels that were richly perfused with red blood cells, as shown in FIG. 1C. Similar differences emerged when the same sections were stained with lectin to visualize endothelial cells. Whereas RasGfp sections contained only solitary lectin-positive cells, the latter surrounded apparent luminal structures in RasGfpMyc neoplasms (FIG. 1C). In contrast, there was no increase in the density of lymphatic vessels, as judged by staining for the lymphatic-specific LYVE-1 marker (FIG. 1C), in spite of the reported propensity of Myc to promote lymphangiogenesis (5).

Example 2

TSR-Encoding mRNAs are Downregulated by Myc

Figure 2A:
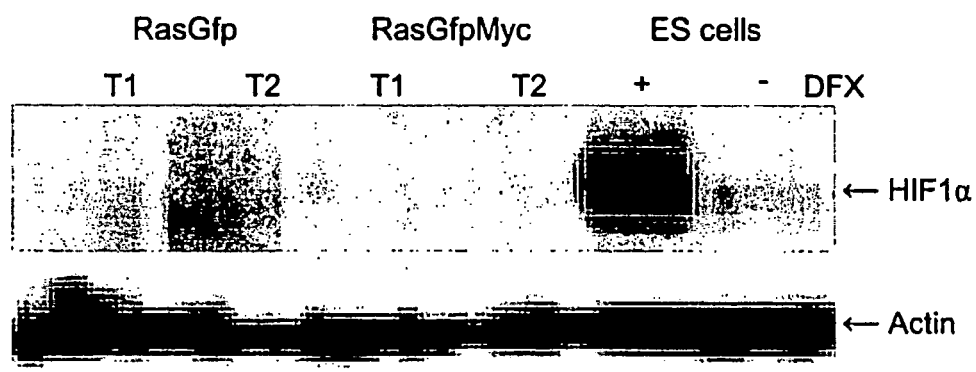
FIGS. 2A-2G show expression of pro- and anti-angiogenic factors in RasGfp and RasGfpMyc carcinomas.
Figure 2B:
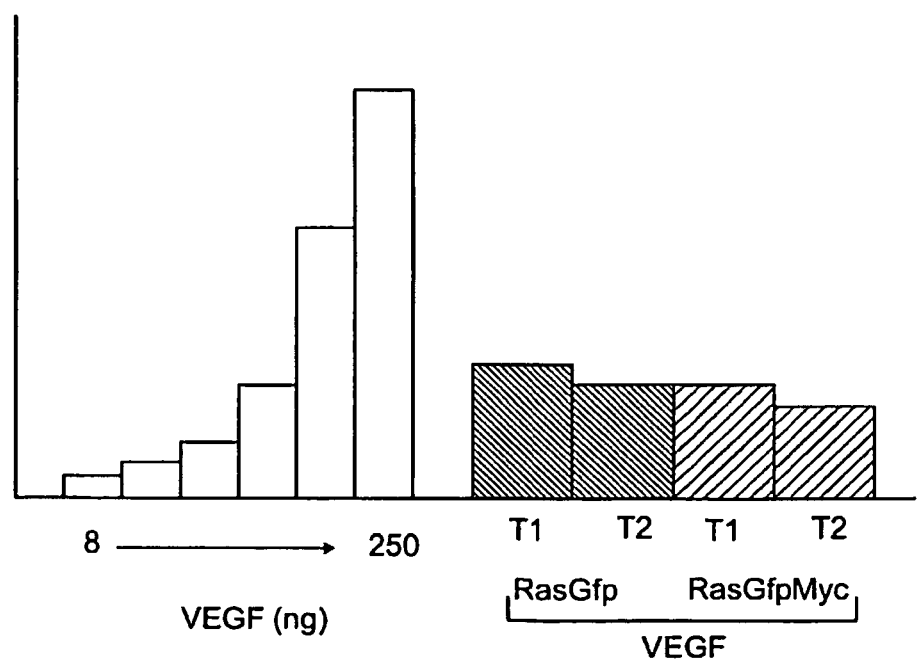

To determine whether the effects of Myc on angiogenesis are mediated by hypoxia, levels of labile hypoxia-induced factor 1a (HIF1a) were assessed in lysates from RasGfp and RasGfpMyc tumors. HIF1a is stable only under hypoxic conditions and was undetectable in either RasGfp or RasGfpMyc tumors, as shown in FIG. 2A. To determine whether hypoxia-activated genes are elevated in RasGfpMyc tumors, microarray analysis was performed on mRNAs from RasGfp and RasGfpMyc tumors. There was no upregulation, at the mRNA level, of a variety of known hypoxia-activated genes such as Slc2a1 (also known as Glut1) or Vegfa. To investigate possible deregulation of VEGF at the protein level, ELISA was performed on tumor cell lysates. No difference was observed in VEGF production between RasGfp and RasGfp-Myc neoplasms (FIG. 2B).

Microarray data was used to analyze the effects of Myc on expression of other pro- and anti-angiogenic molecules. The list of differentially expressed genes with the Gene Ontology (GO) database was compared to determine which of 192 known angiogenesis-related genes are subject to regulation by Myc at the mRNA level. No inducers of angiogenesis were significantly upregulated. However, the list of Myc-down-regulated genes included not only thrombospondin-1, but also other proteins with thrombospondin type 1 repeats (TSR): CTGF, spondin-1 (f-spondin), thrombospondin repeat-containing protein 1, clusterin, SPARC, and thrombospondin type I domain-containing protein 6 (See Table 1, below). Table 1 shows TSR-encoding mRNAs downregulated by Myc. In Table 1, "Fold repression" and "Pvalue" refer to differences in expression levels between the two sets of tumors (RasGfp and RasGfpMyc), per microarray data. The TSR superfamily members SPARC and spondin-1 are known to possess anti-angiogenic properties (12), whereas CTGF can either promote or inhibit angiogenesis (13), depending on developmental context (14).

Figure 2C:
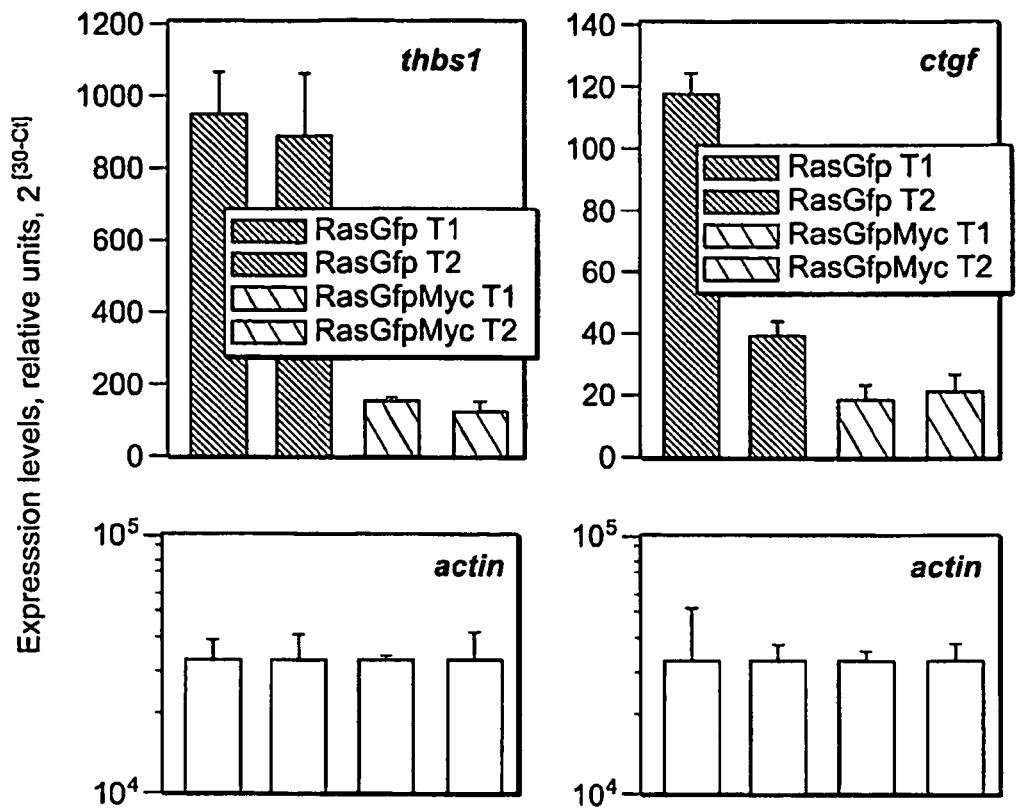
Figure 2D:
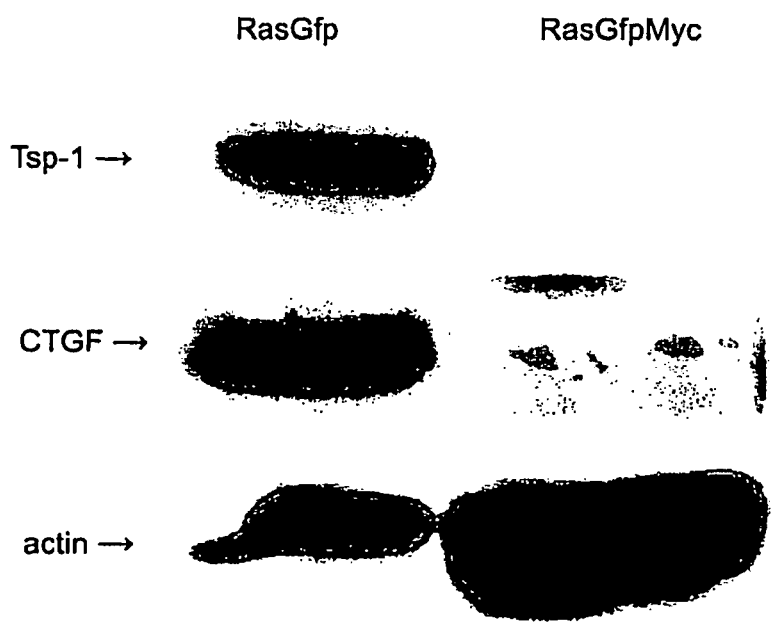
Figure 2E:
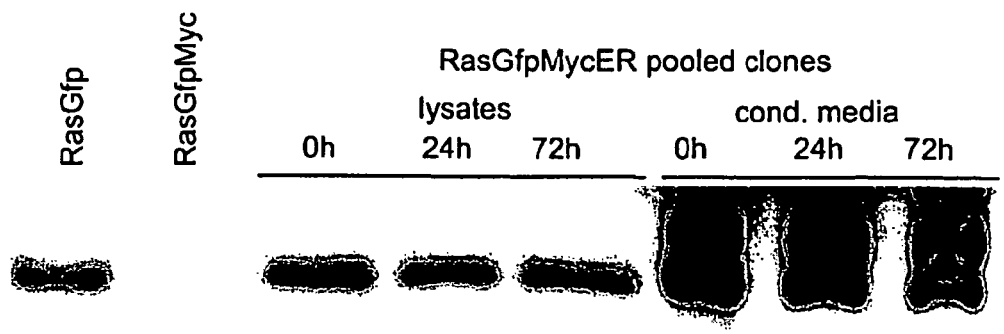
Figure 2F:
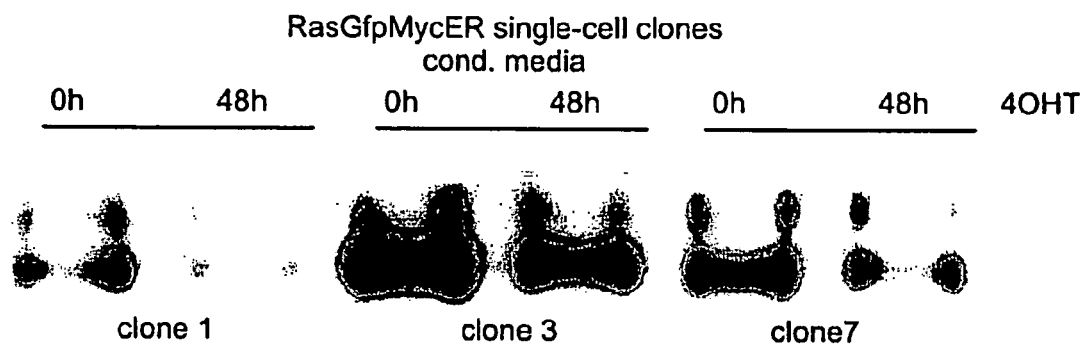
Figure 2G:
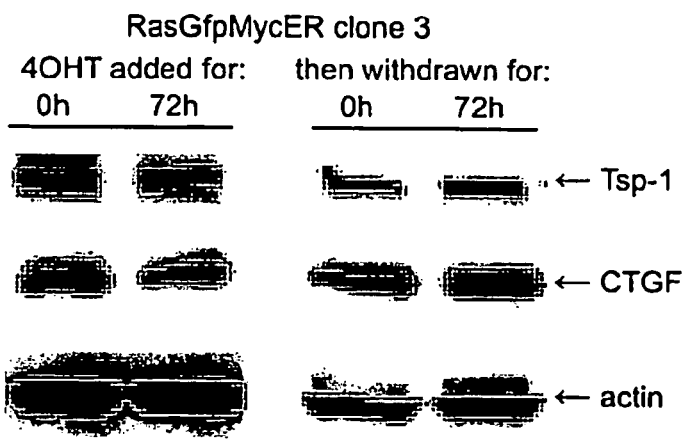

Tsp1 and CTGF data was validated using real-time quantitative RT-PCR (FIG. 2C) and immunoblotting (FIG. 2D). To confirm that their downmodulation is directly related to the overexpression of Myc, CTGF and Tsp1 protein levels were examined in RasGfpMycER cells. Treatment with 4OHT for 24-72 hours resulted in a reduction of CTGF levels in MycER cell lysates and medium conditioned by pooled MycER clones (FIG. 2E). This was also confirmed in several single-cell RasGfpMycER clones with detectable CTGF expression. In all such clones, this protein was downregulated upon 4OHT treatment (FIG. 2F); one clone (#3) was chosen for further analyses. Using this clone, it was confirmed that Tsp1 and CTGF are repressed in the presence of activated MycER and return to basal levels upon subsequent removal of 4OHT (FIG. 2G). Although the repression was less marked than that observed in RasGfpMyc tumors, it indicated that Tsp1 and CTGF are bona fide Myc effectors.

TABLE 1

TSR-encoding mRNAs downregulated by Myc

| Thrombospondin-related proteins | Fold repression | P-value |
| --- | --- | --- |
| spondin-1 (f-spondin) | 8.0 | 0.05 |
| Thrombospondin 1 | 7.7 | 0.006 |

TABLE 1-continued

TSR-encoding mRNAs downregulated by Myc

Figure 3A:
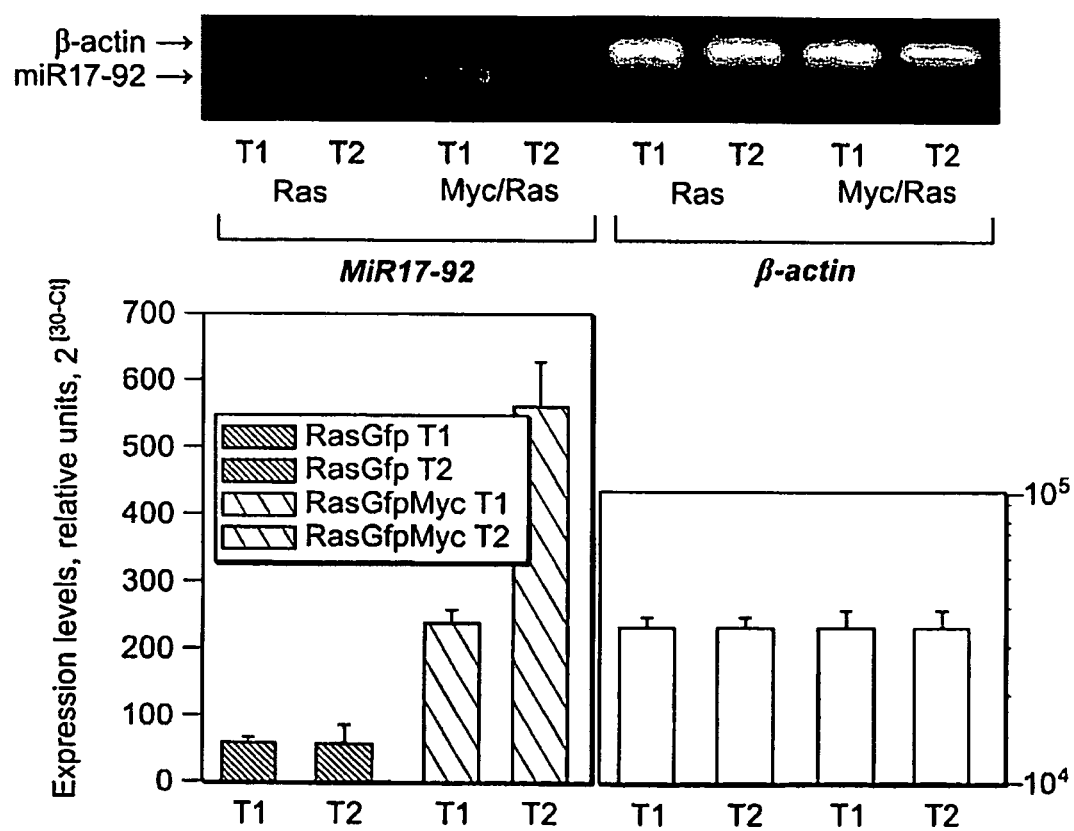
FIGS. 3A-3F show miR-17-92 and TSR protein expression in RasGfp and RasGfpMyc cells.
Figure 3B:
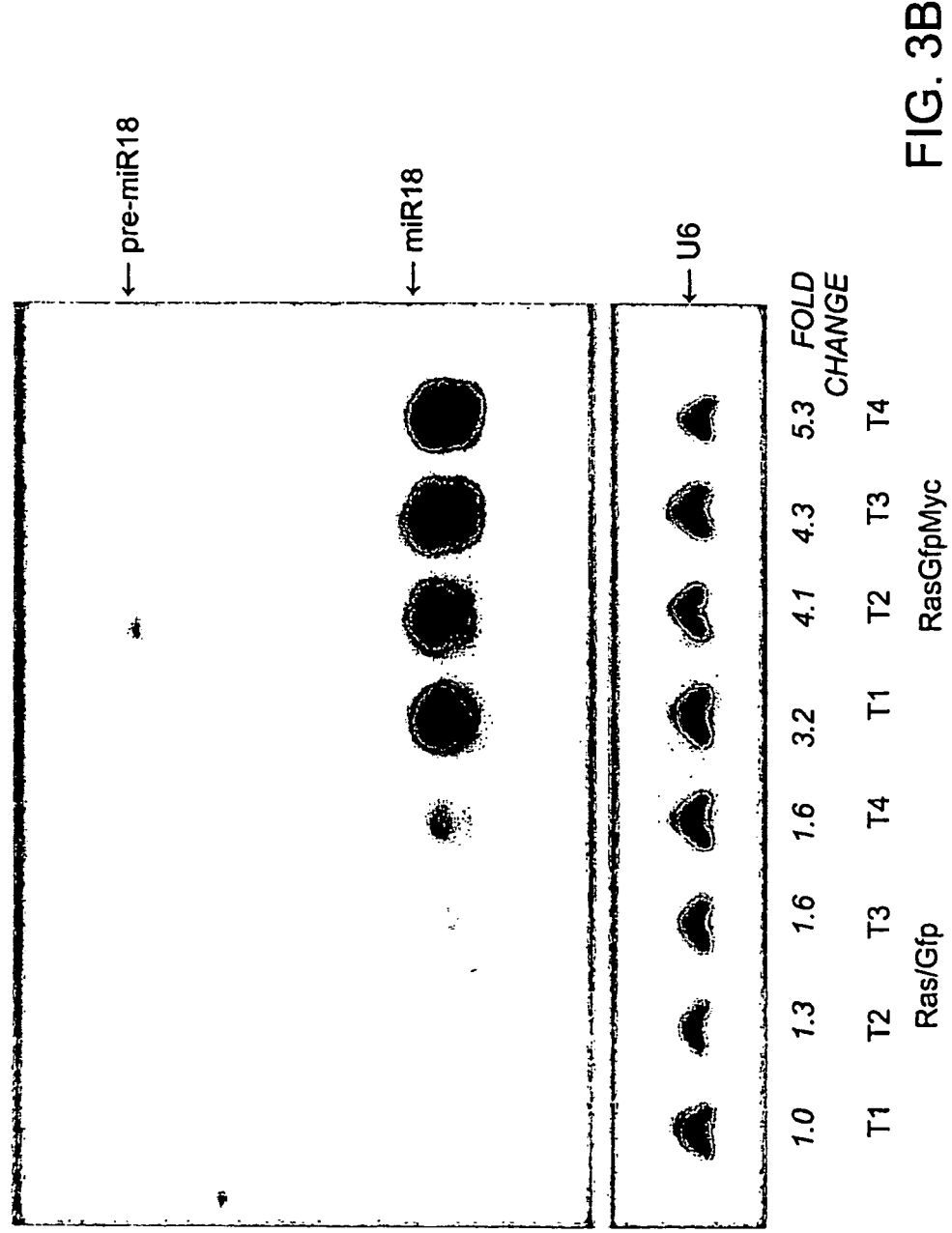

| Thrombospondin-related proteins | Fold repression | P-value |
|---|---|---|
| ADAMTS2 | 7.6 | 0.063 |
| WISP2 | 6.0 | 0.13 | levels of miR-17-92 primary transcript were elevated in the presence of overexpressed Myc (FIG. 3A), as were levels of its cleavage products (such as miR-18a), as shown by RNA blotting in FIG. 3B). Notably, several members of the TSR superfamily are predicted targets of the miR-17-92 cluster (according to the MiRanda algorithm (18)). Table 2, shown below, shows TSR proteins that are predicted targets of the miR17-92 cluster. Myc-target genes are shown in bold.

TABLE 2

TSR proteins that are predicted targets of the miR17-92 cluster

| Gene | Gene Description | Suppressed by Myc at mRNA level | Target of which miRNA | Number of hits | Distance from the start of the 3' UTR | p-value (per Sanger Inst algorithm) |
|---|---|---|---|---|---|---|
| CTGF | Connective tissue growth factor | Yes | miR-19a, b<br>miR-18 | 4 | 1030, 1030<br>1032, 1033 | 0.0015 |
| THSD3 | thrombospondin, type I domain containing 3 isoform 3 | not on array | miR-17-5p<br>miR-20<br>miR-18 | 4 | 1170<br>1171<br>1172, 1173 | |
| ADAMTS18 | A disintegrin and metalloproteinase with Tsp motifs 18 | No | miR-17-5p<br>miR-20<br>miR-19a, b | 4 | 181<br>183<br>235, 236 | |
| ADAMTS12 | A disintegrin and metalloproteinase with Tsp motifs 12 | Yes | miR-19a, b<br>miR-17-3p | 3 | 21, 21<br>26 | |
| THBS1 | Thrombospondin 1 | Yes | miR-18/19 (depending on species) | 2 | 33, 35 | 0.0004 |
| THSD1 | thrombospondin, type I domain containing 1 | not on array | miR-19a, b | 2 | 78, 78 | 0.0003 |
| ADAMTS1 | A disintegrin and metalloproteinase with Tsp motifs 1 | No | miR-20 | 1 | 999 | 0.0007 |
| ADAMTS6 | A disintegrin and metalloproteinase with Tsp motifs 6 | No | miR-18 | 1 | 192 | |
| WISP2 | WNT1 inducible signaling pathway protein 2 | Yes | miR-17-3p | 1 | 89 | 0.0003 |
| BAI3 | Brain-specific angiogenesis inhibitor 3 | Brain-specific | miR-17-3p | 1 | 543 | |

TABLE 1-continued

TSR-encoding mRNAs downregulated by Myc

| Thrombospondin-related proteins | Fold repression | P-value |
|---|---|---|
| Thrombospondin repeat containing [protein] 1 | 5.7 | 0.003 |
| Clusterin | 5.3 | 0.003 |
| CTGF, connective tissue growth factor | 5.0 | 0.001 |
| SPARC (secreted acidic cysteine rich glycoprotein) | 3.3 | 0.1 |
| ADAMTS12 | 3.1 | 0.022 |
| Thrombospondin type I domain containing [protein] 6 | 2.3 | 0.008 |

Example 3

Inhibition of miR-17-92 Cluster microRNAs Restored Expression of Tsp1 and CTGF

It has been previously shown that rather than affecting the thrombospondin-1 promoter, Myc decreases Tsp1 mRNA half-life (8). More recently, microRNAs have emerged as important regulators of mRNA stability (15), and at least one microRNA cluster (miR-17-92) is directly activated by Myc in human lymphocytes (16) and cooperates with Myc during B-lymphomagenesis (17). Its role in promoting growth of solid tumors has not been fully elucidated. Using quantitative RT-PCR analysis, it was determined that the steady-state levels of miR-17-92 primary transcript were elevated in the presence of overexpressed Myc (FIG. 3A), as were levels of its cleavage products (such as miR-18a), as shown by RNA blotting in FIG. 3B).

Figure 3C:
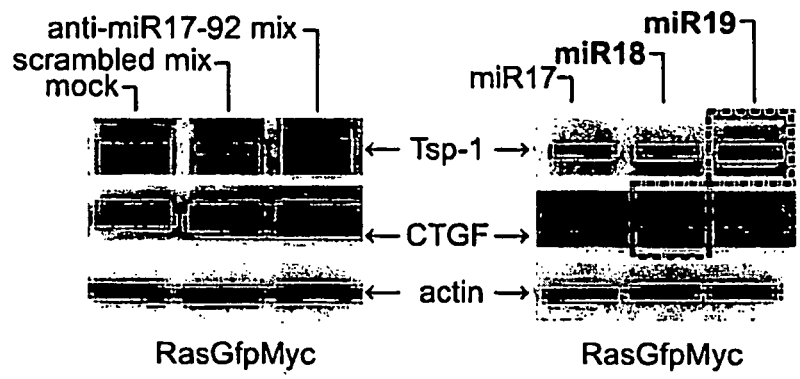

A further question was to determine whether Myc-induced upregulation of the miR-17-92 cluster is directly responsible for the downregulation of TSR proteins in RasGfpMyc cells. As microRNA function can be inhibited with specific 2'-O-methyl oligoribonucleotides (19); TSR protein expression in transiently transfected RasGfpMyc cells was examined. Using a mixture of antisense oligoribonucleotides targeting six microRNAs from the miR-17-92 cluster, expression of Tsp1 and CTGF in RasGfpMyc cells was partly restored (FIG. 3C, left). Transfection of antisense oligonucleotides to individual microRNAs further suggested that within the cluster, miR-19 is primarily responsible for Tsp1 downregulation and miR-18 for CTGF downregulation in response to Myc (FIG. 3C). Antisense oligonucleotides to miR-17-5p (FIG. 3C), miR-20 and miR-92 did not affect TSR protein levels, consistent with bioinformatic predictions (see Table 2).

Figure 3D:
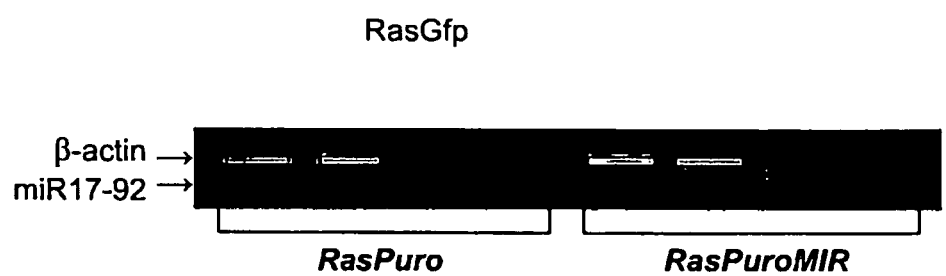
Figure 3E:
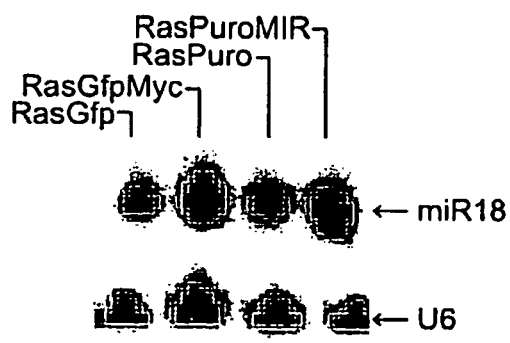
Figure 3F:
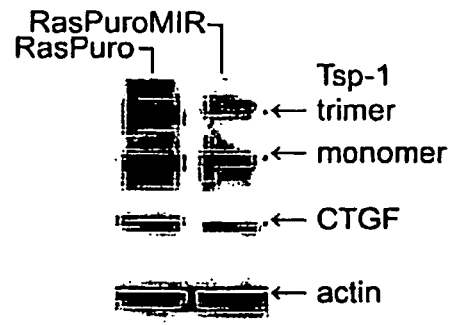

Using retrovirus transduction, Ras cells overexpressing the human miR-17-92 cluster ('RasPuroMIR', FIG. 3D) were generated, which upon cleavage yield microRNAs that are identical to their mouse counterparts. The level of their overexpression was physiological; that is, comparable to that attained in RasGfpMyc cells (FIG. 3E). As predicted, RasPuroMIR cells produced lower levels of thrombospondin-1 and especially CTGF, as compared with vector-transduced RasPuro cells (FIG. 3F). In the case of CTGF, a 90% reduction in mRNA levels was observed, indicative of regulation at the level of mRNA turnover.

Example 4 miR-17-92 Modulates Tumor Neovascularization

Figure 4A:
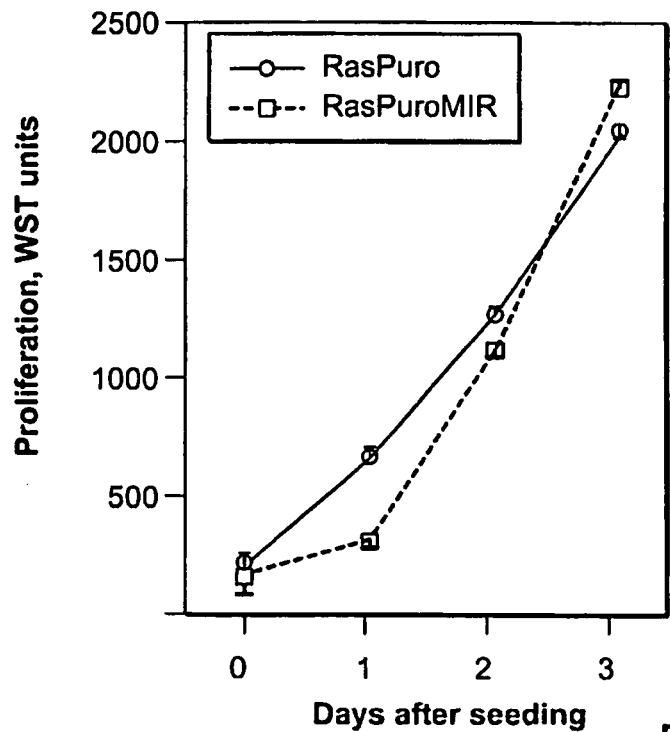
FIGS. 4A-4E show the effects of miR-17-92 upregulation in Ras-only cells on neoplastic growth.
Figure 4B:
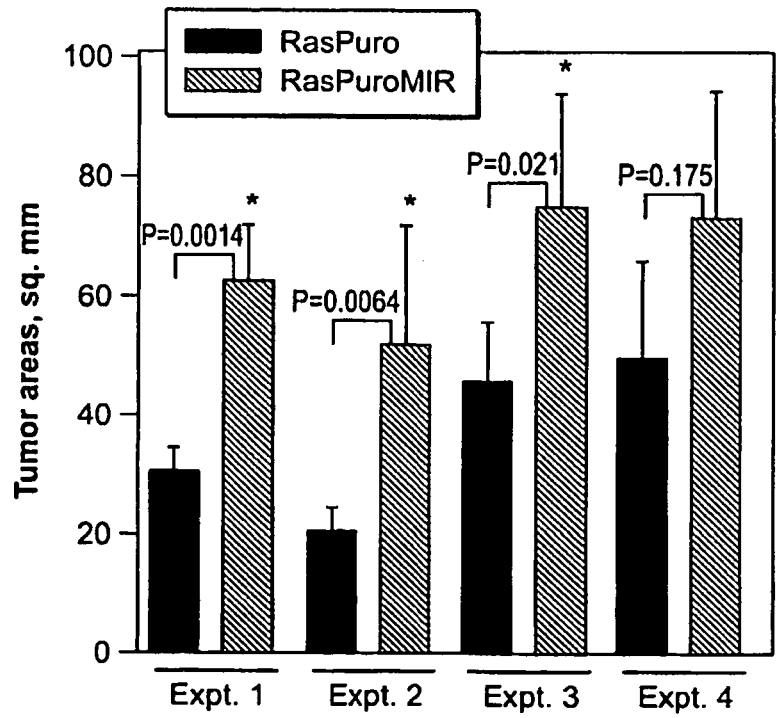
Figure 4C:
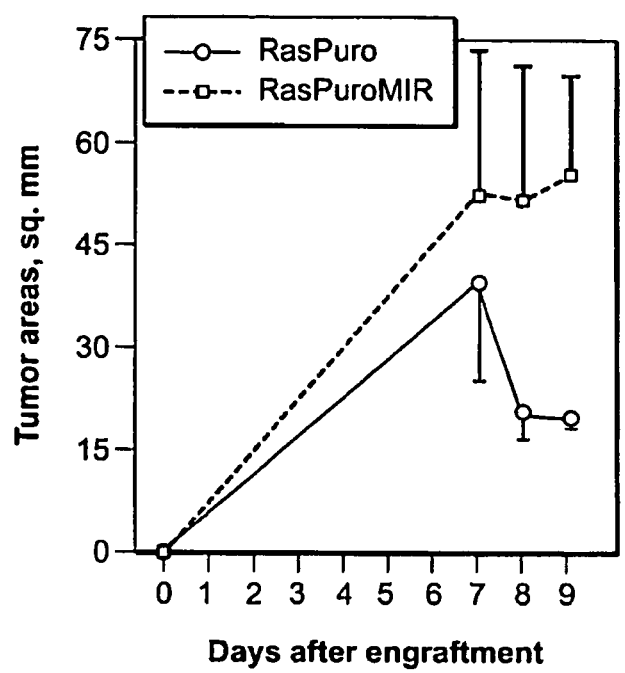
Figure 4D:
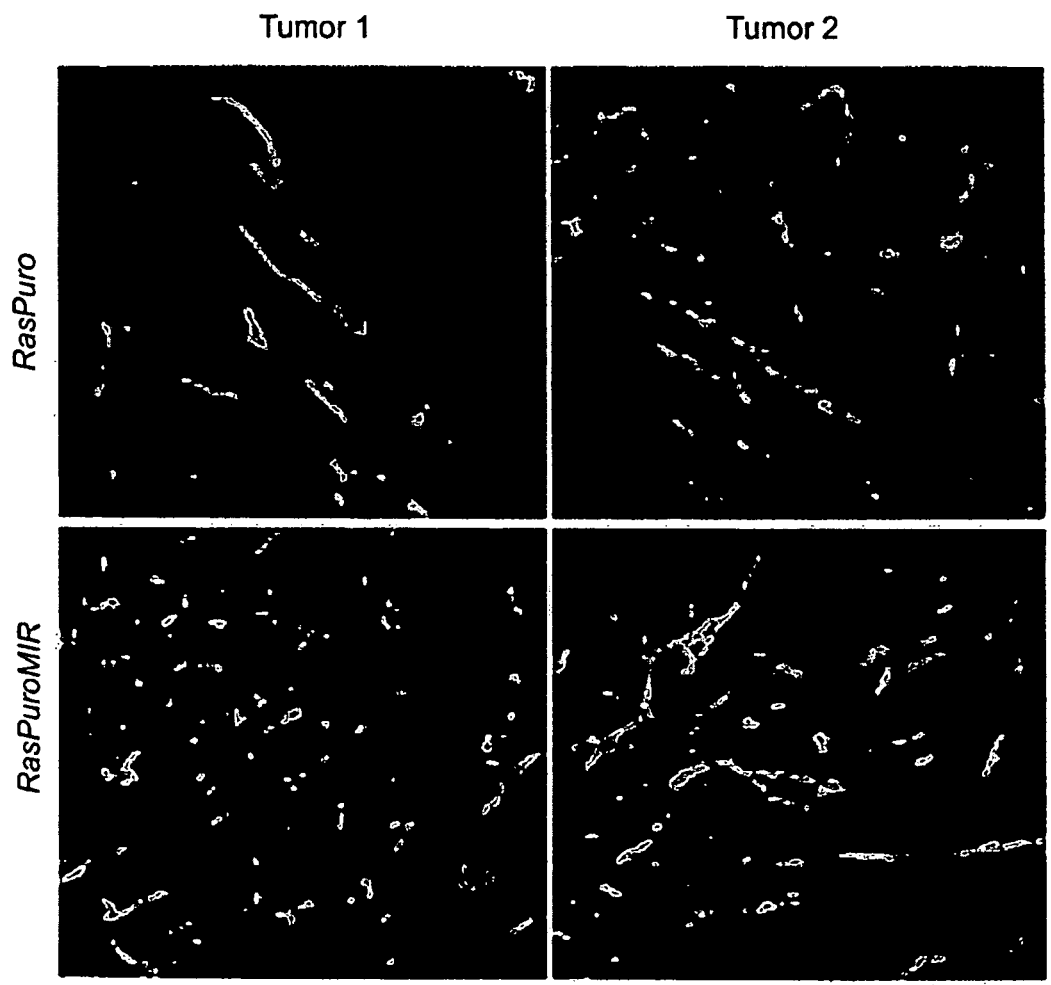
Figure 4E:

Next, it was examined whether overexpression of miR-17-92 could partly recapitulate Myc-induced phenotypes and confer non-cell-autonomous advantages to RasPuroMIR cells. The water-soluble tetrazolium-1 (WST) assay was used to determine that in vitro RasPuro and RasPuroMIR cells grow at a similar rate, as shown in FIG. 4A. However, when cells were implanted into C57BL6/NCr mice, RasPuroMIR cells formed tumors that were on average 1.6-2.5 times larger than RasPuro tumors (data from four independent experiments, as shown in FIG. 4B). By monitoring tumor kinetics, it was determined that the two sets of neoplasms initially grew at similar rates but diverged when they were several millimeters in diameter, a recognized threshold for angiogenic tumors (20). At that time point, only RasPuroMIR cells were capable of progressive growth, whereas RasPuro tumors stagnated or even slightly regressed (FIG. 4C, data from experiment 2 in FIG. 4B; similar observations were made in experiments 1, 3 and 4). To examine the effects of miR-17-92 overexpression on tumor vasculature, tumor-bearing mice were injected intravenously with FITC-conjugated lectin and sacrificed 20 minutes later. In numerous sections examined using confocal microscopy, RasPuroMIR tumors exhibited a higher density of perfused vessels, as shown in FIG. 4D. Moreover, when the same cells were embedded in Matrigel and injected them subcutaneously into syngeneic hosts, RasPuroMIR cells promoted more vigorous neovascularization, as judged by hemoglobin assay. In particular, only RasPuroMIR implants contained large-caliber vascular channels reminiscent of RasGfpMyc tumors (FIG. 4E).

Although Myc contributes to angiogenesis in one-hit model neoplasms (1-4), its involvement in angiogenesis is uncertain in the case of tumors (for example, colon carcinomas) in which Myc is coactivated with Ras and in which mutations in the TP53 tumor suppressor gene are common. Both activation of Ras and inactivation of p53 are considered pro-angiogenic. Besides being the repressors of thrombospondin-1, H-Ras and K-Ras are known to upregulate VEGF and increase the activity of matrix metalloproteinases (MMP) required for endothelial cell migration (reviewed in ref. 21). The ability of Ras to promote angiogenesis has been documented in a transgenic tumor setting (22). The loss of p53 may result in improved stability of hypoxia-induced factor alpha (HIF1a) (23), as well as upregulation of VEGF and downregulation of Tsp1 (24).

In the results presented herein, a combination of mutations in K-ras and Trp53 mutations yielded indolent, poorly vascularized tumors. It was not before Myc overexpression and a further decrease in TSR protein levels that robust tumor vasculature developed, greatly boosting overall neoplastic growth. Profound downregulation of Tsp1 and CTGF might stem from both acute and delayed effects of Myc. In short-term experiments with MycER-transduced cells, in which only acute effects are assessed, Tsp1 and CTGF were downregulated 65%-80%. Approximately the same level of repression was apparent in miR-17-92-transduced Ras-cells. Thus, activation of the miR-17-92 cluster can account for the acute effects of Myc on TSR protein expression. Additional delayed effects could stem from the propensity of Myc to activate certain metalloproteinases (25) and thus indirectly affect extracellular proteins.

The data presented herein demonstrates that miR-17-92 can affect non-cell-autonomous processes, such as tumor neovascularization. This indicates that antisense-based microRNA targeting, an emerging therapeutic technology (19,29), is likely to be effective even against apoptosis-resistant tumors. It is possible that activation of the miR-17-92 pathway may not be the sole pro-angiogenic event triggered by Myc. However, even partial restoration of TSR expression could tip the balance between pro- and anti-angiogenic factors in favor of the latter. This shift might afford significant therapeutic benefits in colon carcinomas, which are known to respond well to anti-angiogenic therapies (30).

Example 5

Figure 5A:
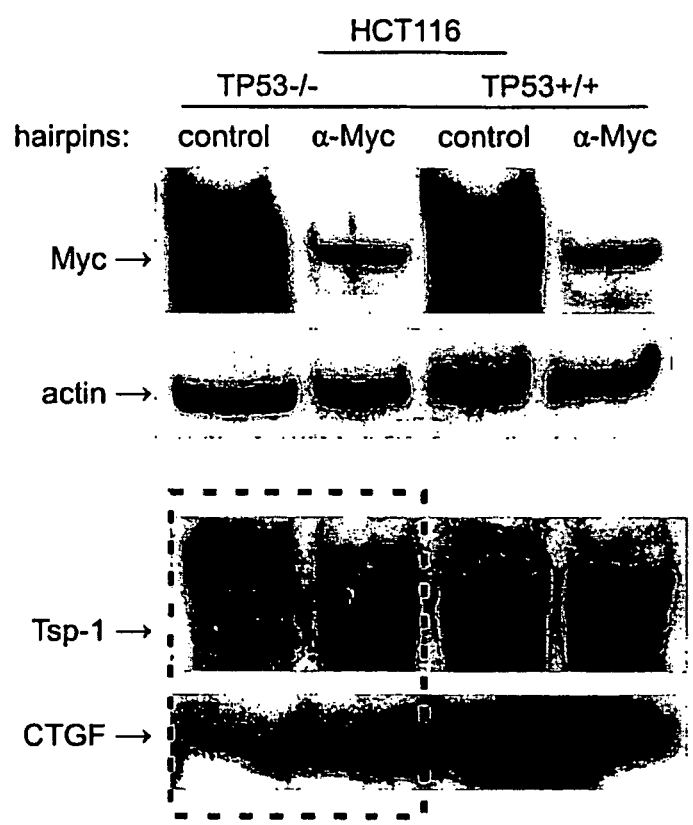
FIGS. 5A-5C show the interplay between My; miR-17-92, and TSR proteins in human colon carcinoma cells.
Figure 5B:
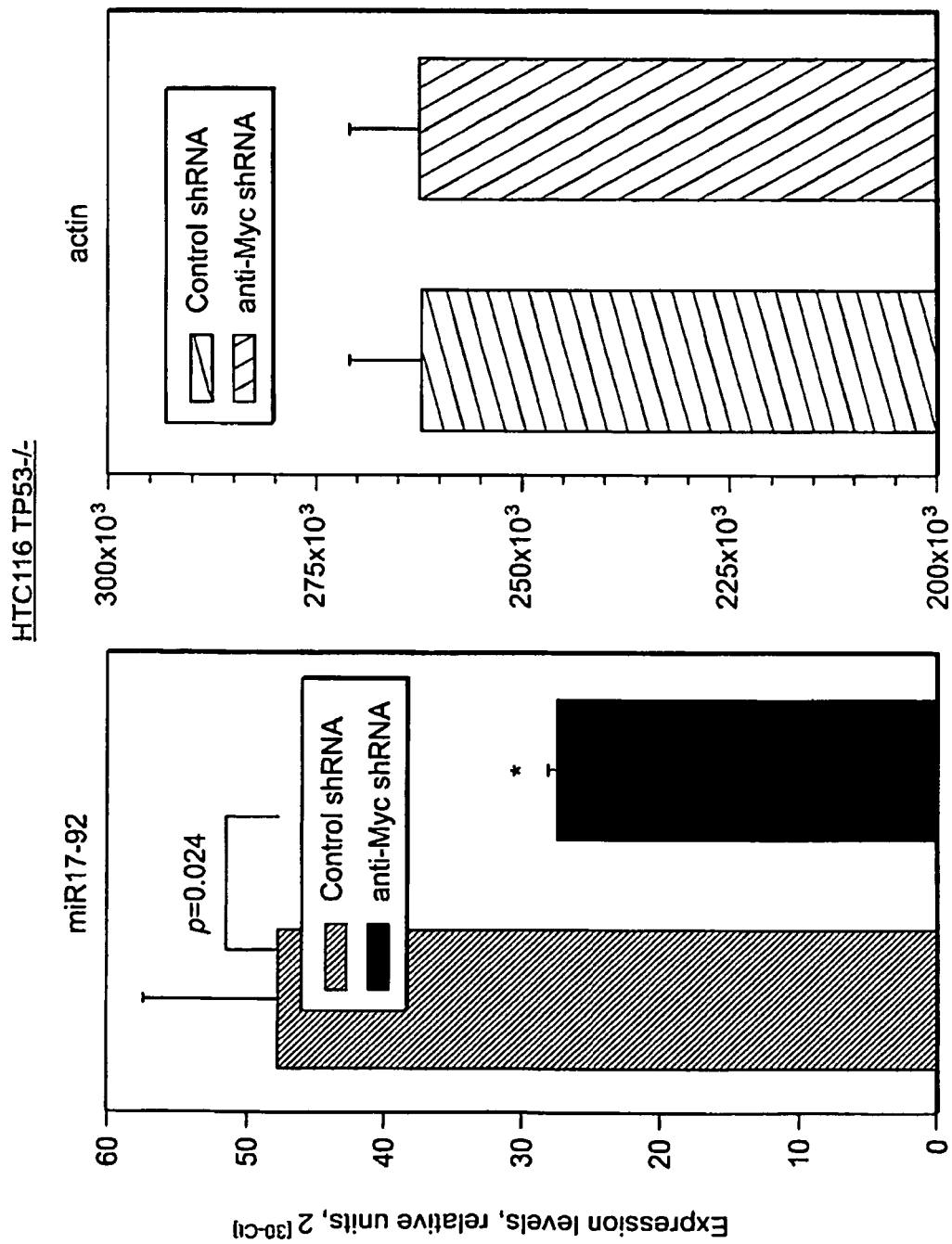

Interplay Between Myc, miR-17-92, and TSR Proteins Occurs in Human Colon Cancer Cell Lines To demonstrate that Myc down-regulates miR-17-92 and TSR proteins in human colon cancer cell lines, HCT116•TP53−/− human colon carcinoma cells were employed because they bear the same genetic lesions as the murine carcinomas previously used in experiments by the inventors: activated Ras, overexpressed Myc, and loss of p53. The cells were infected using lentivirus-encoded anti-Myc hairpins from the Sigma MISSION collection. The efficiency of infection approached 100% (data with control GFP-encoding lentivirus, not shown). As demonstrated in FIG. 5A, transduction with the hairpin #1377 stably decreases Myc levels by at least 10-fold in both HCT116•TP53−/− and HCT116•TP53+/+ cells, as compared to transduction with a control hairpin In HCT116•TP53−/− cells, this leads to upregulation of thrombospondin-1 (FIG. 5A, lanes within red rectangle). Interestingly, in HCT116-TP53+/+ basal thrombospondin-1 levels were higher, consistent with it being a p53 target gene (Dameron et al., 1994). However, these levels didn't increase further upon Myc knockdown. Using the same cells and real-time PCR, it was next demonstrated that Myc knockdown also brings about a decrease in miR-17-92 primary transcript level (FIG. 5B).

Figure 5C:
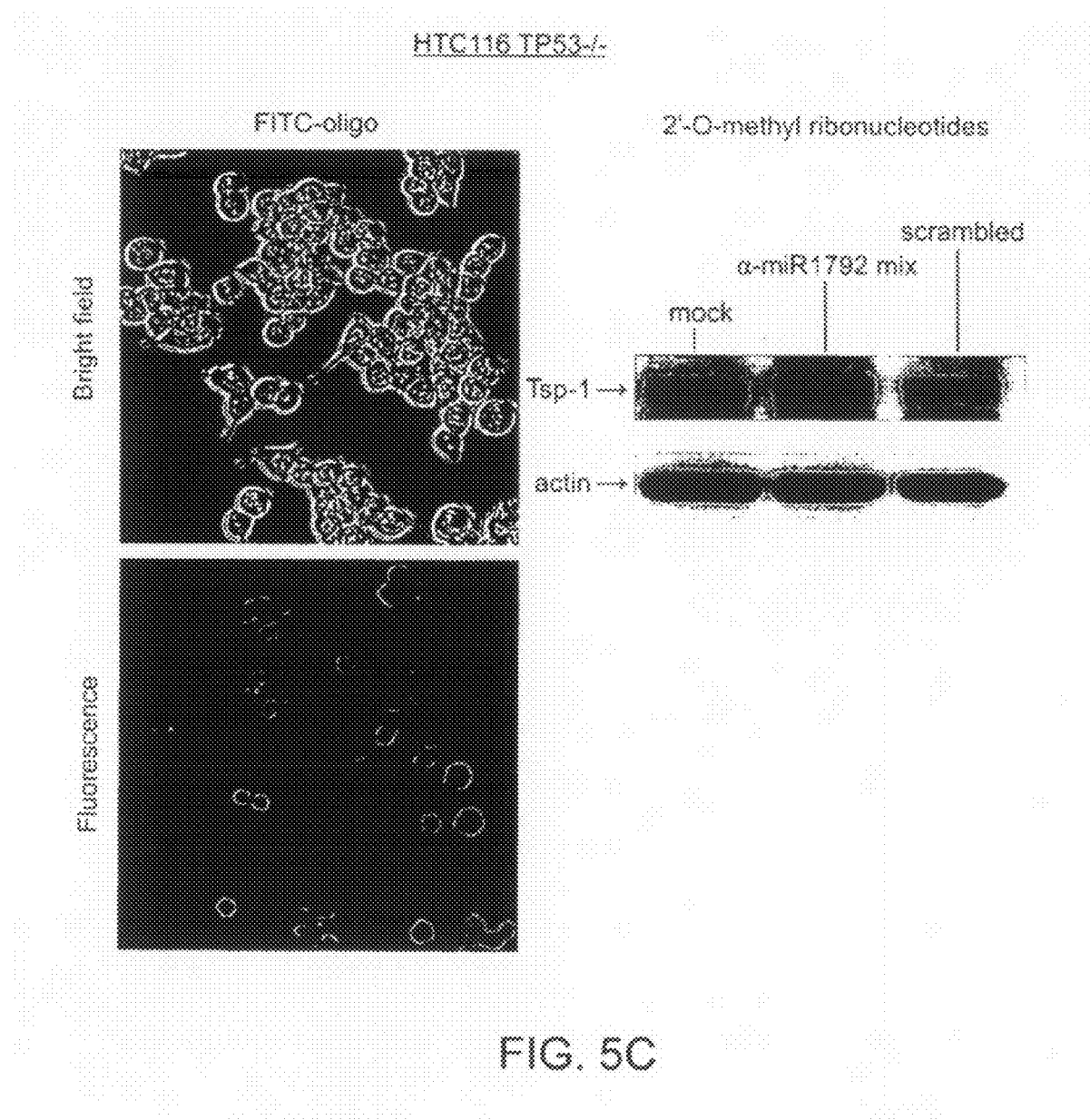

To determine whether HCT116•TP53−/− cells are suitable for transient transfection with antisense 2'-O-methyl oligoribonucleotides against miR-17-92, a control FITC-labeled oligonucleotide was used. At least 50% of cells transfected took up Lipofectamine-coated oligonucleotides (FIG. 5C, left). Moreover, when a mixture of actual 2'-O-methyl oligoribonucleotides was transfected, partial relief of thrombospondin-1 repression was observed (FIG. 5C, right). Thus, all three elements of the Myc-miR-17-92-TSR "triangle" are present in human cells as well.

Figure 6A:
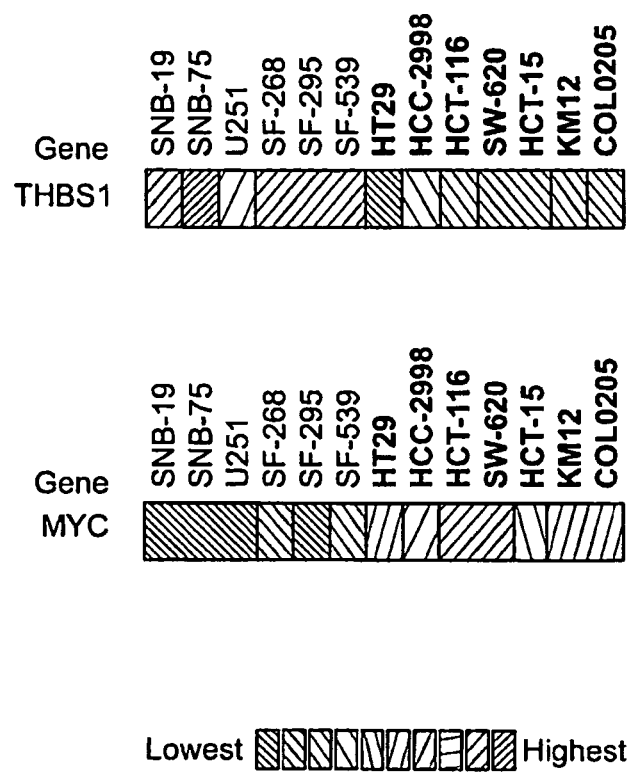
FIGS. 6A-6B show concerted deregulation of Tsp1 and Myc in human colon carcinomas and colon cancer cell lines.
Figure 6B:
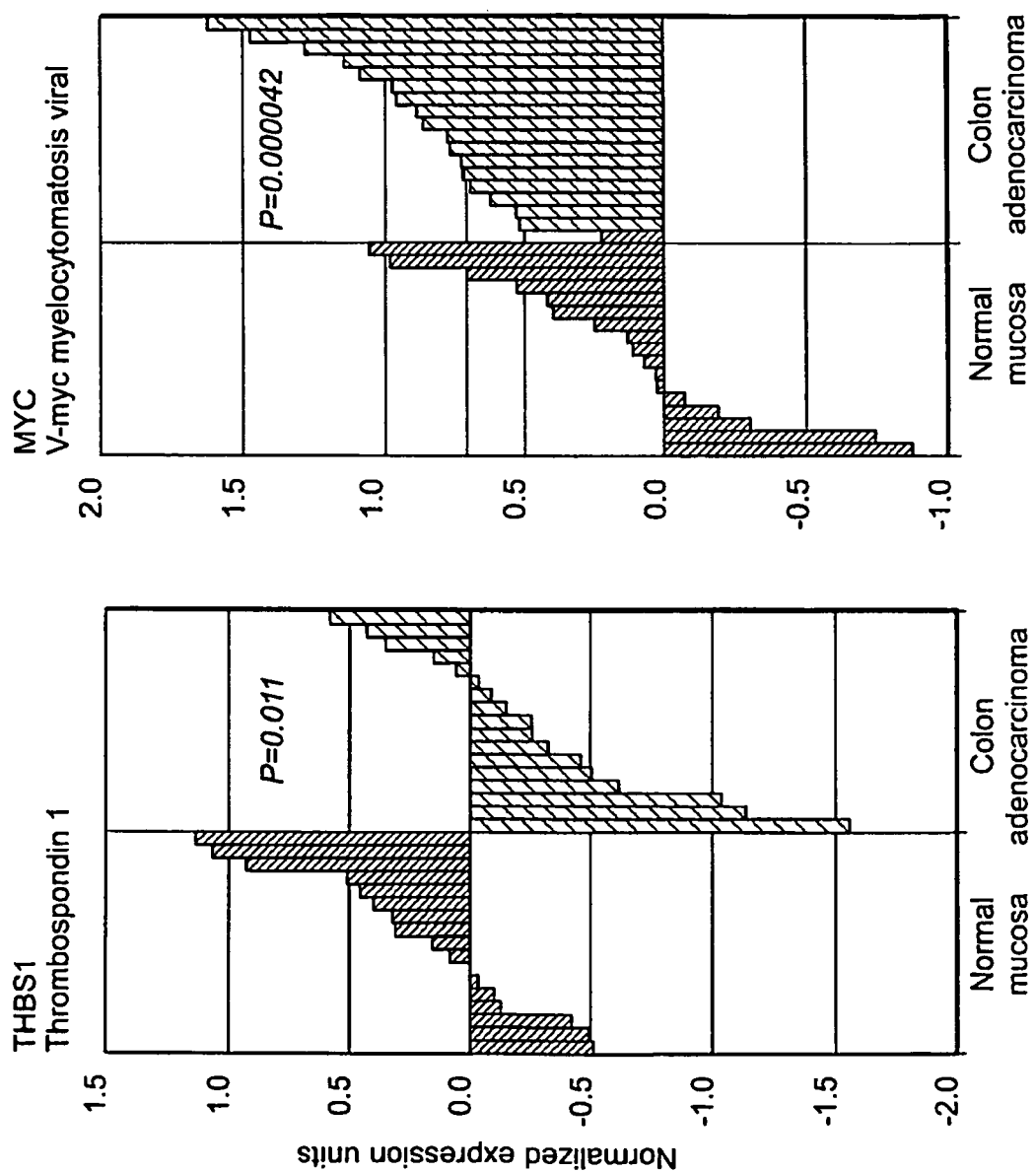

These results indicate that repression of TSR proteins is a prerequisite for neovascularization and aggressive growth of naturally occurring colon carcinomas. To determine if this is indeed the case, two publicly available microarray databases were analyzed (Cancer Gene Anatomy project and Oncomine) and searched for patterns of differential expression of Myc and TSR proteins. Data from both databases indicated that spontaneous human adenocarcinomas have higher levels of Myc and lower levels of thrombospondin-1 mRNAs when compared to normal mucosa (FIG. 6A and FIG. 6B). This is not the case in all neoplastic tissues. For example, thrombospondin-1 is expressed at high levels in lines derived from CNS tumors, where Myc levels are generally low (FIG. 6A excerpt from data on "NCl-60" cells lines)

Figure 7:
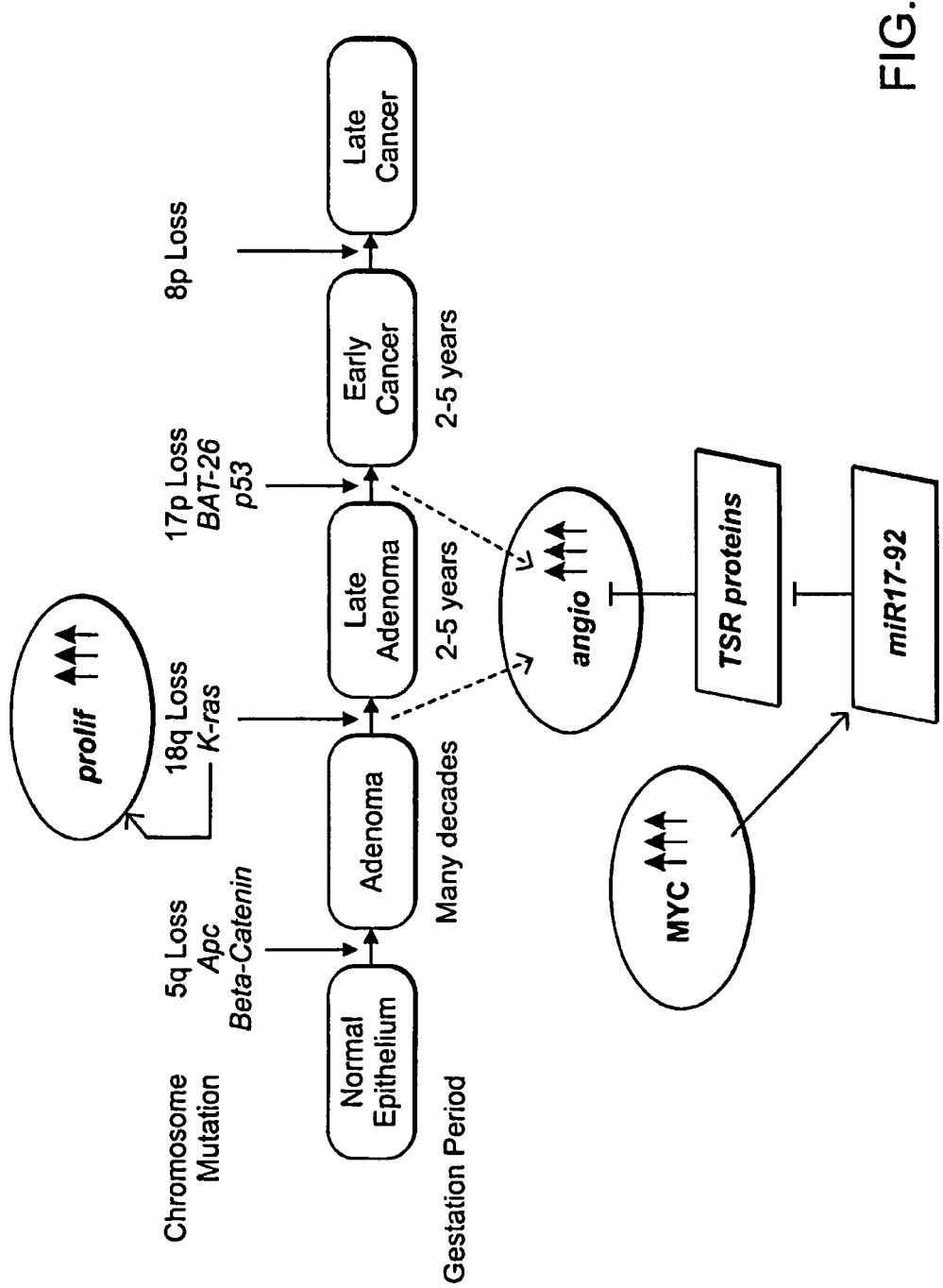
FIG. 7 is a schematic diagram that illustrates the role of Myc in colon carcinoma neovascularization. Through upregulation of miR-17-92 and ensuing down-regulation of TSR proteins, Myc enhances tumor angiogenesis ("angio"). In this setting, Ki-Ras is chiefly responsible for cell proliferation ("prolif") although both Ras and p53 contribute to tumor angiogenesis (dotted lines.)

The inverse correlation between Myc and thrombospondin-1 levels in naturally occurring tumors (FIG. 6B) indicates that even in genetically complex colon carcinomas bearing ki-ras and p53 mutations, myc is still required for robust tumor angiogenesis. Furthermore, Myc's contribution to neovasculatization is related to the down-regulation of thrombospondin-1 and other TSR proteins via post-transcriptional mechanisms involving up-regulation of the MIR-17-92 microRNA cluster (FIG. 7).

Although Myc contributes to angiogenesis in one-hit model neoplasms (1-4), its involvement in angiogenesis is uncertain in the case of tumors (for example, colon carcinomas) in which Myc is coactivated with Ras and in which mutations in the TP53 tumor suppressor gene are common. Both activation of Ras and inactivation of p53 are considered pro-angiogenic. Besides being the repressors of thrombospondin-1, H-Ras and K-Ras are known to upregulate VEGF and increase the activity of matrix metalloproteinases (MMP), which is required for endothelial cell migration (reviewed in ref. 21). The ability of Ras to promote angiogenesis has been documented in a transgenic tumor setting (22). The loss of p53 may result in improved stability of hypoxia-induced factor alpha (HIF1a) (23), as well as upregulation of VEGF and downregulation of Tsp1 (24).

In the results presented herein, a combination of mutations in K-ras and Trp53 mutations yielded indolent, poorly vascularized tumors. It was not before Myc overexpression and a further decrease in TSR protein levels that robust tumor vasculature developed, greatly boosting overall neoplastic growth. Profound downregulation of Tsp1 and CTGF might stem from both acute and delayed effects of Myc. In short-term experiments with MycER-transduced cells, in which only acute effects are assessed, Tsp1 and CTGF were down-regulated 65%-80%. Approximately the same level of repression was apparent in miR-17-92-transduced Ras-cells. Thus, activation of the miR-17-92 cluster can account for the acute effects of Myc on TSR protein expression. Additional delayed effects could stem from the propensity of Myc to activate certain metalloproteinases (25) and thus indirectly affect extracellular proteins.

The data presented herein demonstrates that miR-17-92 can affect non-cell-autonomous processes, such as tumor neovascularization. This indicates that antisense-based microRNA targeting will be effective against difficult to treat apoptosis-resistant tumors. Even if the activation of the miR-17-92 pathway is not the sole pro-angiogenic event triggered by Myc, partial restoration of TSR expression is expected to reduce angiogenesis and treat or prevent the onset of colon cancer, including but not limited to pre-malignant colon lesions, such as non-invasive tumors or polyps.

The above results were obtained using the following methods and materials.

Cell Lines and Tumor Production p53-null colonocytes transformed with retroviruses encoding K-Ras, Myc and MycER have been described previously (10,11). To obtain doubly transduced cells, MigR1 retroviral vectors encoding either Myc or the Myc-estrogen receptor fusion were transfected into GP293 cells using Lipofectamine 2000 (Invitrogen) along with plasmids encoding viral proteins: gag-pol (pGP) and VSV-G protein from vesicular stomatitis virus. Viral supernatants were harvested 48-72 hours later and added to recipient cells. Polybrene was added to cells to facilitate infection. GFP-positive cells were obtained using FACS.

The mouse stem cell virus-based vector (MSCV) encoding miR-17-92 has been described previously (16). MSCV-miR-17-92-transduced cells were obtained using puromycin selection. C57BL6/NCr mice were obtained from the US National Cancer Institute. Transformed colonocytes were implanted either subcutaneously or orthotopically, into the wall of the cecum. For 4-hydroxytamoxifen via sonication, in corn oil (Sigma) at the concentration of 10 mg/ml. 4-OHT was administered daily by intraperitoneal injection at the dose of 1 mg per mouse. Cultured cells expressing MycER were exposed to 250 nM 4-OHT dissolved in ethanol.

Antisense Inhibition of miR-17-92 Cluster

2'-O-methyl oligoribonucleotides were synthesized by Integrated DNA Technologies (see sequences in Table 3 below). For the analysis of CTGF and Tsp1 protein levels, a mixture of 2'-O-methyl oligoribonucleotides (100 pmol each) targeting individual members of the cluster or 600 pmol of the scrambled oligoribonucleotide were transfected into RasGf-pMyc colonocytes growing in six-well dishes (plated at 200,000 cells per well 24 h before transfection) using Lipofectamine 2000. Transfection efficiency (495%) was confirmed using BLOCK-iT Fluorescent Oligo (Invitrogen). Protein lysates were collected 48 hours after transfection and analyzed by immunoblotting.

TABLE 3

Sequences of qRT-PCR primers and 2'-O-methyl oligoribonucleotides

| Gene | Sense oligo | Antisense oligo |
|---|---|---|
| qRT-PCR primers | | |
| Thrombospondin 1 | AAGCGCCTATTTACTTCCCACTAG | TCCTTTCTTTGACATGCCTGAA |
| CTGF | CACCTAAAATCGCCAAGCCTG | AGTTCGTGTCCCTTACTTCCTG |
| murine miR-17-92 (primary transcript) | ACGCACTTGTTCAGTTCCG | TAGTAACCCACCCCCATTCC |
| humaan miR-17-92 (primary transcript) | CTGTCGCCCAATCAAACTG | GTCACAATCCCCACCAAAC |
| β-actin | TTCGTTGCCGGTCCACA | ACCAGCGCAGCGATATCG |
| 2'-O-methyl oligoribonucleotides | | |
| miR-17-5p | | ACUACCUGCACUGUAAGCACUUUG |
| miR-18a | | UAUCUGCACUAGAUGCAC CUUA |
| miR-19a | | UCAGUUUUGCAUAGAUUUGCACA |

TABLE 3-continued

Sequences of qRT-PCR primers and
2'-O-methyl oligoribonucleotides

| Gene | Sense oligo | Antisense oligo |
|---|---|---|
| miR-19b-1 | | UCAGUUUUGCAUGGAUUUGCACA |
| miR-20a | | CUACCUGCACUAUAAGCACUUUA |
| miR-92-1 | | CAGGCCGGGACAAGUGCAAUA |
| miR-scrambled | | AAAACCUUUUGACCGAGCGUGUU |

Analyses of Tumor Specimens and Blood Vasculature

Tumor sizes were measured using calipers and tumor weights were recorded on the day of tumor excision. Levels of VEGF in protein extracts were determined by ELISA (R&D Systems), using a purified VEGF standard. Alternatively, tissues were fixed in formalin, embedded in paraffin, sectioned and subjected to histological staining or immunohistochemistry. Vascular endothelial cells were stained using the Bandeiraea simplicifolia lectin (BS-1; Sigma). Lymphatics were visualized using a 1:500 dilution of rabbit polyclonal antibody to LYVE-1 (Research Diagnostics), a biotinylated secondary antibody, and avidin-linked peroxidase. Images were captured at 20× magnification using a Nikon Eclipse E600 microscope and a Photometrix CoolSnap camera.

To detect perfused blood vessels, tumor-bearing mice were injected intravenously with 100 ml of 2 mg/ml FITC-conjugated Lycopersicon esculentum lectin (Vector Labs) 20 minutes before being killed. After excision, tumors were embedded in OCT (Fisher Scientific), frozen in liquid nitrogen, and sectioned into thick (50-mm) sections using a cryostat. Slides were examined using an upright Zeiss Axiovert 200M microscope equipped with a Zeiss LSM510 V is/UV META confocal system. FITC fluorescence was detected by a 30 mW argon laser system. Images were viewed through a 10× objective, and serial images were acquired at 2-mm intervals using LSM510 META V3.2 software. Images were integrated to create a composite projection of a vessel in three dimensions. The in vivo Matrigel neovascularization assay has been described in detail earlier (3).

Microarray and microRNA Target Analyses

RNA from RasGfp and RasGfpMyc tumors was used. cDNAs were synthesized using in vitro transcription with biotinylated CTP and UTP. Labeled cDNAs were hybridized to the Mouse Genome 430 2.0 Array chip (Affymetrix) using the University of Pennsylvania Microarray Facility standard protocol (available on the world wide web at www.med.upenn.edu/microarr/Data%20Analysis/Affymetrix/methods.htm). Affymetrix MAS5 probe set signals and presence/absence flags were calculated. The Local Pooled Error (LPE) test for differential expression as implemented in S+ArrayAnalyzer v 1.1 (Insightful Corporation) was applied with 1% Bonferroni multiple testing correction to median interquartile range-normalized MAS 5 signal values. The resulting lists were imported into GeneSpring v 6.1 (Silicon Genetics), filtered for Presence (per Affymetrix MAS5 analysis) in two of two samples in one or more conditions (RasGfp or RasGfpMyc) and then filtered for a change of at least 60%.

The comparison with the Gene Ontology database lists was carried out using DAVID 2.0 software, as implemented at the website apps1.niaid.nih.gov/david/. Putative miR-17-92 targets were identified using the MiRanda algorithm 18, as implemented at http://www.microrna.org and http://microrna.sanger.ac.uk.

Protein and RNA Blotting

For thrombospondin-1 and CTGF expression analysis, either cell lysates or conditioned medium were used. Myc and HIF1a expression was detected in cell lysates. Membranes were probed with antibodies to Tsp1 (Ab-11, Lab Vision), CTGF (L-20, Santa Cruz Biotechnology), Myc (N-262/sc-764, Santa Cruz Biotechnology) and HIF1a (NB 100-105; Novus Biologicals) diluted according to manufacturers' recommendations. Conditioned medium was loaded on PAGE without dilution. Appropriate secondary antibodies were used in horseradish peroxidase-conjugated forms (Amersham Biosciences). Antibody binding was detected using the enhanced chemiluminescence system (Amersham). When indicated, a monoclonal antibody reactive with mouse $\beta$-actin (Sigma) was used to confirm equal loading. Detection of mouse miR-17-92 RNAs using RNA blotting was performed as described in ref. 16.

Real-Time PCR

Total RNAs were isolated using TRI Reagent (Sigma) and treated with a TURBO DNA-free kit (Ambion). cDNAs were prepared from 2 mg RNA using the SuperScript First-Strand Synthesis System for RT-PCR (Invitrogen). The nucleotide sequences of primers used are provided in Table 1, above. Amplifications were performed using Smartcycler (Cepheid). Typical conditions were as follows:

95 1C for 150 s (one cycle), then 95 1C for 10 s and 60 1C for 30 s (30 cycles).

All reactions were performed in duplicates or triplicates to ensure accuracy of quantification.

Accession Codes

Microarray data described herein have been deposited to the ArrayExpress (on the world wide web at www.ebi.ac.uk/arrayexpress) database under accession number E-MEXP-757, which is hereby incorporated by reference in its entirety.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

LITERATURE CITED

1. Pelengaris, S., Littlewood, T., Khan, M., Elia, G. & Evan, G. I. Reversible activation of c-Myc in skin: induction of a complex neoplastic phenotype by a single oncogenic lesion. Mol. Cell 3, 565-577 (1999).
2. Brandvold, K. A., Neiman, P. & Ruddell, A. Angiogenesis is an early event in the generation of myc-induced lymphomas. Oncogene 19, 2780-2785 (2000).
3. Ngo, C. et al. An in vivo function for the transforming myc protein: elicitation of the angiogenic phenotype. Cell Growth Differ. 11, 201-210 (2000).
4. Baudino, T. A. et al. c-Myc is essential for vasculogenesis and angiogenesis during development and tumor progression. Genes Dev. 16, 2530-2543 (2002).
5. Ruddell, A., Mezquita, P., Brandvold, K. A., Farr, A. & Iritani, B. M. B lymphocyte specific c-Myc expression stimulates early and functional expansion of the vasculature and lymphatics during lymphomagenesis. Am. J. Pathol. 163, 2233-2245 (2003).
6. Knies-Bamforth, U. E., Fox, S. B., Poulsom, R., Evan, G. I. & Harris, A. L. c-Myc interacts with hypoxia to induce angiogenesis in vivo by a vascular endothelial growth factor dependent mechanism. Cancer Res. 64, 6563-6570 (2004).
7. Tikhonenko, A. T., Black, D. J. & Linial, M. L. Viral Myc oncoproteins in infected fibroblasts down-modulate thrombospondin-1, a possible tumor suppressor gene. J. Biol. Chem. 271, 30741-30747 (1996).
8. Janz, A., Sevignani, C., Kenyon, K., Ngo, C. & Thomas-Tikhonenko-Tikhonenko, A. Activation of the Myc oncoprotein leads to increased turnover of thrombospondin-1 mRNA. Nucleic Acids Res. 28, 2268-2275 (2000).
9. Watnick, R. S., Cheng, Y. N., Rangarajan, A., Ince, T. A. & Weinberg, R. A. Ras modulates Myc activity to repress thrombospondin-1 expression and increase tumor angiogenesis. Cancer Cell 3, 219-231 (2003).
10. Sevignani, C. et al. Tumorigenic conversion of p53-deficient colon epithelial cells by an activated Ki-Ras gene. J. Clin. Invest. 101, 1572-1580 (1998).
11. Thomas-Tikhonenko-Tikhonenko, A. et al. Myc-transformed epithelial cells down-regulate clusterin which inhibits their growth in vitro and carcinogenesis in vivo. Cancer Res. 64, 3126-3136 (2004).
12. Tucker, R. P. The thrombospondin type 1 repeat superfamily. Int. J. Biochem. Cell Biol. 36, 969-974 (2004).
13. Inoki, I. et al. Connective tissue growth factor binds vascular endothelial growth factor (VEGF) and inhibits VEGF-induced angiogenesis. FASEB J. 16, 219-221 (2002).
14. Perbal, 13. CCN proteins: multifunctional signalling regulators. Lancet 363, 62-64 (2004).
15. Hwang, H. W. & Mendell, J. T. MicroRNAs in cell proliferation, cell death, and tumorigenesis. Br. J. Cancer 94, 776-780 (2006).
16. O'Donnell, K. A., Wentzel, E. A., Zeller, K. I., Dang, C. V. & Mendell, J. T. c-Myc-regulated microRNAs modulate E2F1 expression. Nature 435, 839-843 (2005).
17. He, L. et al. A microRNA polycistron as a potential human oncogene. Nature 435, 828-833 (2005).
18. John, B. et al. Human microRNA targets. PLoS Biol. 2, e363 (2004).
19. Meister, G., Landthaler, M., Dorsett, Y. & Tuschl, T. Sequence-specific inhibition of microRNA- and siRNA-induced RNA silencing. RNA 10, 544-550 (2004).
20. Kerbel, R. S. & Folkman, J. Clinical translation of angiogenesis inhibitors. Nat. Rev. Cancer 2, 727-739 (2002).
21. Rak, J., Yu, J. L., Kerbel, R. S. & Coomber, B. L. What do oncogenic mutations have to do with angiogenesis/vascular dependence of tumors? Cancer Res. 62, 1931-1934 (2002).
22. Chin, L. et al. Essential role for oncogenic Ras in tumour maintenance. Nature 400, 468-472 (1999).
23. Ravi, R. et al. Regulation of tumor angiogenesis by p53-induced degradation of hypoxia-inducible factor 1 alpha. Genes Dev. 14, 34-44 (2000).
24. Dameron, K. M., Volpert, O. V., Tainsky, M. A. & Bouck, N. Control of angiogenesis in fibroblasts by p53 regulation of thrombospondin-1. Science 265, 1582-1584 (1994).
25. Himelstein, B. P., Lee, E. J., Sato, H., Seiki, M. & Muschel, R. J. Transcriptional activation of the matrix metalloproteinase-9 gene in an H-ras and v-myc transformed rat embryo cell line. Oncogene 14, 1995-1998 (1997).
26. Esquela-Kerscher, A. & Slack, F. J. Oncomirs—microRNAs with a role in cancer. Nat. Rev. Cancer 6, 259-269 (2006).
27. Volinia, S. et al. A microRNA expression signature of human solid tumors defines cancer gene targets. Proc. Natl. Acad. Sci. USA 103, 2257-2261 (2006).
28. Hayashita, Y. et al. A polycistronic microRNA cluster, miR-17-92, is overexpressed in human lung cancers and enhances cell proliferation. Cancer Res. 65, 9628-9632 (2005).
29. Krutzfeldt, J. et al. Silencing of microRNAs in vivo with 'antagomirs'. Nature 438, 685-689 (2005).
30. Hurwitz, H. et al. Bevacizumab plus irinotecan, fluorouracil, and leucovorin for metastatic colorectal cancer. N. Engl. J. Med. 350, 2335-2342 (2004).

What is claimed is:

1. A method of reducing angiogenesis in a subject in need thereof, the method comprising contacting a cell with an effective amount of an antisense nucleic acid molecule complementary to at least a portion of a microRNA nucleic acid molecule of the mir-17-92 cluster, wherein the antisense nucleic acid molecule comprises a nucleobase sequence having at least 95% identity to a sequence selected from the group consisting of:

```
                                    (SEQ ID NO: 1)
miR-17-5p:   ACUACCUGCACuGUAAGCACUUUG;

(SEQ ID NO: 2)
mir-18a:     UAUGUGCACUAGAUGCACCUUA;

(SEQ ID NO: 3)
mir-19a:     UCAGUUUUGCAUAGAUUUGCACA;

(SEQ ID NO: 4)
mir-19b:     UCAGUUUUGCAUGGAUUUGCACA;

(SEQ ID NO: 5)
mir-20a:     CUACCUGCACUAUAAGCACUUUA;
and (SEQ ID NO: 6)
mir-92-1:    CAGGCCGGGACAAGUGCAAUA.
``` thereby reducing angiogenesis.

2. The method of claim 1, wherein the antisense nucleic acid molecule decreases the expression of the microRNA in the cell.

3. The method of claim 1, wherein the cell is present in a tissue or organ.

4. The method of claim 1, wherein the cell is a neoplastic cell.

5. The method of claim 1, wherein the cell is an ocular cell.

6. The method of claim 1, wherein microRNA is mir-19.

7. The method of claim 1, wherein the microRNA is mir-18.

8. The method of claim 1, wherein the antisense nucleic acid molecule is an siRNA.

9. A method for increasing the expression of a thrombospondin type 1 repeat (TSR) protein in a cell, the method comprising contacting the cell with an effective amount of an antisense nucleic acid molecule complementary to at least a portion of a microRNA nucleic acid molecule of the mir-17-92 cluster, wherein the antisense nucleic acid molecule comprises a nucleobase sequence having at least 95% identity to a sequence selected from the group consisting of:

```
miR-17-5p:                              (SEQ ID NO: 1)
ACUACCUGCACuGUAAGCACUUUG;

mir-18a:                                (SEQ ID NO: 2)
UAUCUGCACUAGAUGCACCUUA;

mir-19a:                                (SEQ ID NO: 3)
UCAGUUUUGCAUAGAUUUGCACA;

mir-19b:                                (SEQ ID NO: 4)
UCAGUUUUGCAUGGAUUUGCACA;

mir-20a:                                (SEQ ID NO: 5)
CUACCUGCACUAUAAGCACUUUA;
and mir-92-1:                               (SEQ ID NO: 6)
CAGGCCGGGACAAGUGCAAUA,
``` thereby increasing the expression of a TSR protein.

10. The method of claim 9, wherein the method increases expression of thrombospondin 1 (Tsp 1) or connective tissue growth factor (CTGF) relative to a control.

11. A method of treating an ocular disease characterized by increased angiogenesis in a subject in need thereof, the method comprising administering to the subject an effective amount of an antisense nucleic acid molecule complementary to at least a portion of a microRNA nucleic acid molecule of the mir-17-92 cluster, wherein the antisense nucleic acid molecule comprises a nucleobase sequence having at least 95% identity to a sequence selected from the group consisting of:

```
miR-17-5p:                              (SEQ ID NO: 1)
ACUACCUGCACuGUAAGCACUUUG;

mir-18a:                                (SEQ ID NO: 2)
UAUCUGCACUAGAUGCACCUUA;

mir-19a:                                (SEQ ID NO: 3)
UCAGUUUUGCAUAGAUUUGCACA;

mir-19b:                                (SEQ ID NO: 4)
UCAGUUUUGCAUGGAUUUGCACA;

mir-20a:                                (SEQ ID NO: 5)
CUACCUGCACUAUAAGCACUUUA;
and mir-92-1:                               (SEQ ID NO: 6)
CAGGCCGGGACAAGUGCAAUA,
``` thereby treating an ocular disease.

\* \* \* \* \*

SEQUENCE LISTING

```
<160> NUMBER OF SEQ ID NOS: 17

<210> SEQ ID NO 1
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
acuaccugca cuguaagcac uuug                                            24
```

```
<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uaucugcacu agaugcaccu ua                                                 22

<210> SEQ ID NO 3
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ucaguuuugc auagauuugc aca                                                23

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ucaguuuugc auggauuugc aca                                                23

<210> SEQ ID NO 5
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cuaccugcac uauaagcacu uua                                                23

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
caggccggga caagugcaau a                                                  21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagcgcctat ttacttccca ctag                                               24

<210> SEQ ID NO 8
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cacctaaaat cgccaagcct g                                              21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgcacttgt tcagttccg                                                 19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctgtcgccca atcaaactg                                                 19

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttcgttgccg gtccaca                                                   17

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcctttcttt gacatgcctg aa                                             22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agttcgtgtc ccttacttcc tg                                             22

<210> SEQ ID NO 14
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
tagtaaccca cccccattcc                                                    20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtcacaatcc ccaccaaac                                                     19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accagcgcag cgatatcg                                                      18

<210> SEQ ID NO 17
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaaccuuuu gaccgagcgu guu                                                23
```